US008664273B2

(12) United States Patent (10) Patent No.: US 8,664,273 B2
McNair et al. (45) Date of Patent: *Mar. 4, 2014

(54) TREATMENT OF HEPATITIS C VIRUS WITH TELAPREVIR (VX-950) IN PATIENTS NON-RESPONSIVE TO TREATMENT WITH PEGYLATED INTERFERON-ALPHA 2A/2B AND RIBAVIRIN

(75) Inventors: Lindsay McNair, Allston, MA (US); John McHutchison, Woodside, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/153,199

(22) Filed: Jun. 3, 2011

(65) Prior Publication Data

US 2012/0045415 A1 Feb. 23, 2012

Related U.S. Application Data

(63) Continuation of application No. 12/910,589, filed on Oct. 22, 2010, now abandoned, which is a continuation of application No. PCT/US2009/002526, filed on Apr. 23, 2009.

(60) Provisional application No. 61/047,336, filed on Apr. 23, 2008, provisional application No. 61/060,008, filed on Jul. 30, 2008, provisional application No. 61/099,452, filed on Sep. 23, 2008, provisional application No. 61/109,805, filed on Oct. 30, 2008, provisional application No. 61/152,535, filed on Feb. 13, 2009, provisional application No. 61/161,681, filed on Mar. 19, 2009.

(51) Int. Cl.
*A61K 38/21* (2006.01)
*A61K 38/00* (2006.01)
*A61K 31/14* (2006.01)

(52) U.S. Cl.
USPC ........... 514/588; 514/4.3; 514/894; 424/85.7; 424/85.4

(58) Field of Classification Search
None
See application file for complete search history.

(56) References Cited

U.S. PATENT DOCUMENTS

2006/0105978 A1* 5/2006 Chu et al. .................. 514/44

OTHER PUBLICATIONS

Vertex Pharmaceutical 10-K filing with the Securities and Exchange Commision, Mar. 16, 2006, pp. 3-5.*
Dash, S., et al., HCV-Hepatocellular Carcinoma: New Findings and Hope for Effective Treatment, Microscopy Research and Technique, 2005, pp. 130-148, vol. 68, Wiley-Liss, Inc.
Wong, W., et al., Update on Chronic Hepatitis C. Clinical Gastroenterology and Hepatology, 2005, pp. 507-520, vol. 3, No. 5, American Gastroenterological Association.
Davis, G. L., Advances in Liver Disease, Highlights from the 55th Annual Meeting of the American Association for the Study of Liver Diseases, Reviews in Gastroenterological Disorders, 2005, pp. 47-61, vol. 5, No. 1, MedReviews, LLC.
Fanning, L. J., Anti-Viral Therapies for Hepatitis C Virus Infection: Current Options and Evolving Candidate Drugs, Letters in Drug Design & Discovery, 2005, pp. 150-161, vol. 2, No. 2, Bentham Science Publishers Ltd.
Pawlotsky, J-M., Therapy of Hepatitis C: From Empiricism to Eradication, Hepatology, Feb. 2006, pp. S207-S220, vol. 43, No. 2, Suppl. 1, American Association for the Study of Liver Diseases.
Shiffman, M. L., Chronic Hepatitis C: Treatment of Pegylated Interferon/Ribavirin Nonresponders, Current Gastroenterology Reports, 2006, pp. 46-52, vol. 8, Current Science, Inc.
Balart, L. A., Advances in Liver Disease, Highlights from the 56th Annual Meeting of the American Association for the Study of Liver Diseases. Reviews in Gastroenterological Disorders, 2006, pp. 48-61, vol. 6, No. 1, MedReviews, LLC.
Sethi, A., et al., Approach to the Management of Patients with Chronic Hepatitis C Who Failed to Achieve Sustained Virologic Response, Infect Dis Clin N Am, 2006, pp. 115-135, vol. 20, Elsevier Inc.
Bacon, B. R., Assessing evidence from clinical trials in chronic hepatitis C. Journal of Viral Hepatitis, 2006, pp. 1-5, vol. 13, Suppl. 1, Blackwell Publishing Ltd.
Thomson, J. A., et al., Hepatitis C virus NS3-4A protease inhibitors: Countering viral subversion in vitro and showing promise in the clinic, Current Opinion in Drug Discovery & Development, 2006, pp. 606-617, vol. 9, No. 5, The Thomson Corporation.
Reesink, H. W., et al., Rapid Decline of Viral RNA in Hepatitis C Patients Treated With VX-950: A Phase Ib, Placebo-controlled, Randomized Study, Gastroenterology, 2006, pp. 997-1002, vol. 131, No. 4, American Gastroenterological Assoc. (AGA) Institute.
Rincon, D., et al., Does interferon improve portal hypertension?, Journal of Antimicrobial Chemotherapy, 2006, pp. 7-12. vol. 58, Oxford University Press on behalf of the British Society for Antimicrobial Chemotherapy.
Lawitz, E. J., et al., 28 Days of the Hepatitis C Protease Inhibitor VX-950, in Combination with PEG-Interferon-Alfa-2a and Ribavirin, is Well-Tolerated and Demonstrates Robust Antiviral Effects, Gastroenterology, Sep. 2006, pp. 950-951, vol. 131, No. 3, AGA Institute.
Schiff, E. R., Emerging strategies for pegylated interferon combination therapy, Nature Clinical Practice, Gastroenterology & Hepatology, Jan. 2007, pp. 517-S21, vol. 4, Supplement 1, Nature Publishing Group.

(Continued)

*Primary Examiner* — Christine J Saoud
*Assistant Examiner* — Jegatheesan Seharaseyon
(74) *Attorney, Agent, or Firm* — Honigman Miller Schwartz & Cohn LLP; Noel E. Day; Jonathan P. O'Brien

(57) ABSTRACT

The present invention relates to antiviral therapies and compositions for treating or preventing Hepatitis C infections in patients and relates to other methods disclosed herein. The invention also relates to kits and pharmaceutical packs comprising compositions and dosage forms. The invention also relates to processes for preparing these compositions, dosages, kits, and packs.

7 Claims, 17 Drawing Sheets

(56) References Cited

OTHER PUBLICATIONS

Kadam, J. S., et al., Changing Treatment Paradigms: Hepatitis C Virus in HIV-Infected Patients, AIDS Patient Care and STDs, HCV Management in HIV/HCV Coinfection, 2007, pp. 154-168, vol. 21, No. 3, Mary Ann Liebert, Inc.

Khokhar, A. S., et al., Future Therapies for Hepatitis C, Current Hepatitis Reports. 2006, pp. 121-128, vol. 5, Current Science Inc.

Shiffman, M. L., Chronic Hepatitis C: Treatment of Pegylated Interferon/Ribavirin Nonresponders, Current Hepatitis Reports, 2005, pp. 114-120, vol. 5, Current Science Inc.

Dusheiko, G., Hepatitis C, Medicine, Liver Infections, 2006, pp. 43-48, vol. 35:1, Elsevier Ltd.

Kaplan, D. E., et al., Propagation of hepatitis C virus infection: Elucidating targets for therapeutic intervention, Drug Discovery Today: Disease Mechanisms, Gastrointestinal disorders, 2006, pp. 471-477, vol. 3, No. 4, Elsevier Ltd.

Cheruvu, S., et al., Advances in Liver Disease, Rev Gastroenterol Disord., 2007, pp. 41-58, vol. 7, No. 1, MedReviews, LLC.

Sulkowski, M., Specific Targeted Antiviral Therapy for Hepatitis C, Current Gastroenterology Reports, Liver, 2007, pp. 5-13, vol. 9, Current Medicine Group LLC.

Pawlotsky, J-M., Treatment of Hepatitis C: Don't Put All Your Eggs In One Baskett, Gastroenterology, Apr. 2007, pp. 1611-1615, vol. 132, No. 4, AGA Institute.

Weigand, K., et al., Treatment of hepatitis C virus infection, World J Gastroenterol, Apr. 7, 2007, pp. 1897-1905, vol. 13, No. 13, The WJG press.

Friedrich-Rust, M., et al., Ultrasound Evaluation of Perihepatic Lymph Nodes During Antiviral Therapy with the Protease Inhibitor Telaprevir (VX-950) in Patients with Chronic Hepatitis C Infection, Ultrasound in Med. & Biol., 2007, pp. 1362-1367, vol. 33, No. 9, World Federation for Ultrasound in Medicine & Biology. USA.

Pawlotsky, J-M., et al., The Hepatitis C Virus Life Cycle as a Target for New Antiviral Therapies, Reviews in Basic and Clinical Gastroenterology, Gastroenterology, 2007, pp. 1979-1998, vol. 132, No. 5, AGA Institute.

Sarrazin, C., et al., Dynamic Hepatitis C Genotypic and Phenotypic Changes in Patients Treated with the Protease Inhibitor Telaprevir, Gastroenterology, 2007, pp. 1767-1777, vol. 132, No. 5, AGA Institute.

Firpi, R. J., et al., Current and Future Hepatitis C Therapies, Archives of Medical Research, 2007, pp. 678-690, vol. 38, Elsevier Inc.

Sheldon, J., et al., Novel protease and polymerase inhibitors for the treatment of hepatitis C virus infection, Expert Opin. Investig. Drugs, 2007, pp. 1171-1181, vol. 16, No. 8, Informa UK Ltd.

Unknown, Introduction, Gastroenterology & Hepatology, Jun. 2007, pp. 3-5, vol. 3, Issue 6, Suppl. 21.

Asselah, T., et al., Management of chronic hepatitis C, Minerva Gastroenterol Dietol, 2007, pp. 9-23, vol. 53, No. 1, Marzo.

Bryan, J., Where next for the treatment of hepatitis C?, Future Virol., 2007, pp. 331-334; vol. 2, No. 4, Future Medicine Ltd.

Chevaliez, S., et al., Inteferon-based therapy of hepatitis C, Advanced Drug Delivery Reviews, 2007, pp. 1222-1241, vol. 59, Elsevier B.V.

Satoskar, R., et al., Retreatment of chronic hepatitis C in previous non-responders and relapsers, Expert Opin. Pharmacother. 2007, pp. 2491-2503, vol. 8, No. 15, Informa UK Ltd.

Keeffe, E. B., Future treatment of chronic hepatitis C, Antiviral Therapy, 2007, pp. 1015-1025, vol. 12, No. 7, International Medical Press.

Garber, K., Hepatitis C: staying the course, Nature Biotechnology, Dec. 2007, pp. 1379-1380, vol. 25, No. 12, Nature Publishing Group.

Keeffe, E. B., Latest Breakthroughs in Chronic Hepatitis B and C, Rev Gastroenterol Disord., 2007, pp. 167-175, vol. 7, No. 3, MedReviews, LLC.

Revill, P., et al., Telaprevir, HCV NS3 Protease Inhibitor Treatment of Hepatitis C, Drugs of the Future, 2007, pp. 786-798, vol. 32, No. 9, Prous Science.

Jacobson, I. M., et al., The Future Use of Combination Therapies to Avoid Viral Resistance and Achieve Sustained Response in Chronic Hepatitis C, Clinical Roundtable Mongraph, Gastroenterology & Hepatology, Dec. 2007, vol. 3, Issue 12, Supplement 34.

Yuan, H.-J., et al., Nonresponse to Treatment for Hepatitis C, Current Management Strategies, Drugs, 2008, pp. 27-42, vol. 68, No. 1, Adis Data Information BV.

Chung, R. T., et al., Mechanisms of Action of Interferon and Ribavirin in Chronic Hepatitis C: Summary of a Workshop, Hepatology, 2006, vol. 47, No. 1, American Association for the Study of Liver Diseases.

Cholongitas, E., et al., Review article: novel therapeutic options for chronic hepatitis C, Aliment Pharmacol Ther, Feb. 2008, pp. 866-884, vol. 27, Blackwell Publishing Ltd.

Montalbano, M., et al., Managing chronic hepatitis C in relapsers and non-responders, Minerva Endocrinal, 2008, pp. 31-47, vol. 54, No. 1, Marzo.

Niederau, C., Aktuelle Therapie der chronischen Hepatitis B und C, Internist, 2008, pp. 1265-1273, vol. 49, Springer Medizin Verlag.

Cross, T. J. S., et al., Current and future management of chronic hepatitis C infection, Postgrad Med J, 2006, pp. 172-176, vol. 84.

Jensen, D. M., et al., Future directions in therapy for chronic hepatitis C, Antiviral Therapy, 2008, pp. 31-36, vol. 13, Suppl. 1, International Medical Press.

Rodriguez-Torres, M., Latinos and Chronic Hepatitis C: A Singular Population, Clinical Gastroenterology and Hepatology, May 2008, pp. 484-490, vol. 6, No. 5, AGA Institute.

Liu-Young, G., et al., Hepatitis C Protease and Polymerase Inhibitors in Development, AIDS Patient Care and STDs, 2006, pp. 1-9, vol. 22, No. 6, Mary Ann Liebert, Inc.

Unknown, Introduction, Gastroenterology & Hepatology, Feb. 2008, pp. 3-5, vol. 4, Issue 2, Suppl. 6.

Balsano, C., Recent Advances in Antiviral Agents: Established and Innovative Therapies for Viral Hepatitis, Mini-Reviews in Medicinal Chemistry, 2008, pp. 307-316, vol. 8, No. 4, Bentham Science Publishers Ltd.

Kronenberger, B., et al., Novel Hepatitis C Drugs in Current Trials, Clin Liver Dis 12, 2008, pp. 529-555, Elsevier Inc.

Unknown, HIV/AIDS and STD Updates, AIDS Patient Care and STDs, 2008, pp. 837-839, vol. 22, No. 10, Mary Ann Liebert, Inc.

Unknown, HIV/AIDS and STD Update, AIDS Patient Care and STDs, 2008, pp. 765-767, vol. 22, No. 9, Mary Ann Liebert, Inc.

Kronenberger, B., et al., Future treatment options for HCV: Double, triple, what is the optimal combination?, Best Practice & Research Clinical Gastroenterology, 2008, pp. 1123-1136, vol. 22, No. 6, Elsevier Ltd.

Unknown, Broad Profile for Telaprevir in Patients with Genotype 1 HCV Infection, HIV/AIDS and STD Updates, AIDS Patient Care, 2009, pp. 68-69, vol. 23, No. 1.

Buti, M., Re-Treatment of Patients with Chronic Hepatitis C and Previously Nonresponsive To Interferon-Based Therapies, Hepatology Rev., 2008, pp. 3-9, vol. 5.

McHutchison, J. G., et al., Results of an Interim Analysis of a Phase 2 Study of Telaprevir (VX-950) with Peginterferon alpha-2a and Ribavirin in Previously Untreated Subjects with Hepatitis C, Late-Breaking Abstracts, J. of Hepatology, 2007, p. S295, vol. 46.

Poordad, F., et al., A Study of Teleprevir (TVR) with PEGinterferon Alfa-2A (P) and Ribavirin (R) in Subjects with Well-Documented Prior P/R Null Response, Non-Responses or Relapse: Preliminary Results, Late-Breaking Abstracts, J. of Hepatology, 2008, p. S374, vol. 48

A Phase 2 Study of Telaprevir (VX-950) in Combination with Peginterferon Alfa-2a (Pegasys®), and Ribavirin (Copegus®) in Subjects with Genotype 1 Hepatitis C who have not achieved Sustained Viral Response With A Prior Course of Interferon Based Therapy, ClinicalTrials.gov archive, Apr. 2, 2007, http://clinicaltrials.gov/archive/NCT00420784/2007_04_02.

* cited by examiner

TREATMENT OF HEPATITIS C VIRUS WITH TELAPREVIR (VX-950) IN PATIENTS NON-RESPONSIVE TO TREATMENT WITH PEGYLATED INTERFERON-ALPHA 2A/2B AND RIBAVIRIN

CROSS-REFERENCE

This application is a continuation of U.S. Nonprovisional application Ser. No. 12/910,589, filed on Oct. 22, 2010, which is a continuation of PCT Application No. PCT/US2009/002526, filed on Apr. 23, 2009, which claims priority to: U.S. Provisional Application No. 61/047,336, filed on Apr. 23, 2008; U.S. Provisional Application No. 61/060,008, filed on Jul. 30, 2008; U.S. Provisional Application No. 61/099,452, filed on Sep. 23, 2008; U.S. Provisional Application No. 61/109,805, filed on Oct. 30, 2008; U.S. Provisional Application No. 61/152,535, filed on Feb. 13, 2009; and U.S. Provisional Application No. 61/161,681, filed on Mar. 19, 2009, the contents of which are incorporated herein by reference in their entireties.

TECHNICAL FIELD OF THE INVENTION

The present invention relates to methods for treating Hepatitis C virus infections in patients non-responsive to treatment with pegylated interferon-alpha-2a/2b and ribavirin (P/R non-responsive).

BACKGROUND OF THE INVENTION

Infection by Hepatitis C virus (HCV) is a compelling human medical problem. HCV is recognized as the causative agent for most cases of non-A, non-B hepatitis, with an estimated human sero-prevalence of 3% globally. Nearly four million individuals may be infected in the United States alone.

Of persons who become infected with HCV, 20-25% may be able to clear the virus after the acute infection, but 75-80% will develop chronic Hepatitis C infection. This usually results in recurrent and progressively worsening liver inflammation, which often leads to more severe disease states such as cirrhosis and hepatocellular carcinoma. Unfortunately, there are no broadly effective treatments for the debilitating progression of chronic HCV.

The HCV genome encodes a polyprotein of 3010-3033 amino acids. The HCV nonstructural (NS) proteins are presumed to provide the essential catalytic machinery for viral replication. The NS proteins are derived by proteolytic cleavage of the polyprotein.

The HCV NS protein 3 (NS3) contains a serine protease activity that helps process the majority of the viral enzymes, and is thus considered essential for viral replication and infectivity. It is known that mutations in the yellow fever virus NS3 protease decreases viral infectivity. The first 181 amino acids of NS3 (residues 1027-1207 of the viral polyprotein) have been shown to contain the serine protease domain of NS3 that processes all four downstream sites of the HCV polyprotein.

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing. HIV protease inhibitors, which inhibit viral protein processing are potent antiviral agents in man, indicating that interrupting this stage of the viral life cycle results in therapeutically active agents. Consequently it is an attractive target for drug discovery.

There are not currently any satisfactory anti-HCV agents or treatments. Until recently, the only established therapy for HCV disease was interferon treatment. The first approved therapy for HCV infection was treatment with standard (non-pegylated) interferon alfa. However, interferons have significant side effects and interferon alfa monotherapy induces long term remission in only a fraction (~25%) of cases. The addition of ribavirin to the treatment regimen increases response rates slightly. Recent introductions of the pegylated forms of interferon (PEG-INTRON® and PEGASYS®), which has also been combined with ribavirin have resulted in only modest improvements in remission rates and only partial reductions in side effects. (PEG refers to polyethyleneglycol.) The current standard of care is a treatment regimen lasting 24-48 weeks, depending on prognostic factors such as HCV genotype and demonstration of initial response to therapy. The majority of HCV genotype-1 patients do not achieve sustained virologic response (SVR) after a 48-week regimen of pegylated interferon-alfa-2a/2b and ribavirin. Moreover, retreatment of prior PR non-responders (null and partial responders) and relapsers with pegylated interferon and ribavirin achieves SVR rates of less than 10% and 30%, respectively. The prospects for effective anti-HCV vaccines remain uncertain.

Thus, there is a need for anti-HCV therapies and appropriate dose regimens for anti-HCV compounds.

HCV and other diseases and disorders are associated with liver damage. There is also a need for therapies and appropriate dose regimens for treating liver damage.

Dosing regimens for VX-950 are described in PCT Publication Numbers WO 2006/050250 and WO 2008/144072, which are incorporated herein by reference in their entirety. Additional dosing regimens for VX-950 are described in PCT Serial Number PCT/US2008/012460, filed on Nov. 4, 2008, which is incorporated herein by reference in its entirety.

SUMMARY OF THE INVENTION

The present invention provides a treatment for Hepatitis C virus infections in P/R non-responsive patients. The invention therefore provides for the prevention of the clinical sequelae of Hepatitis C viral infections. The present invention also provides a treatment for liver damage and liver inflammation.

All of the documents cited herein, are incorporated herein by reference in their entireties.

DETAILED DESCRIPTION OF THE INVENTION

Figure 1:
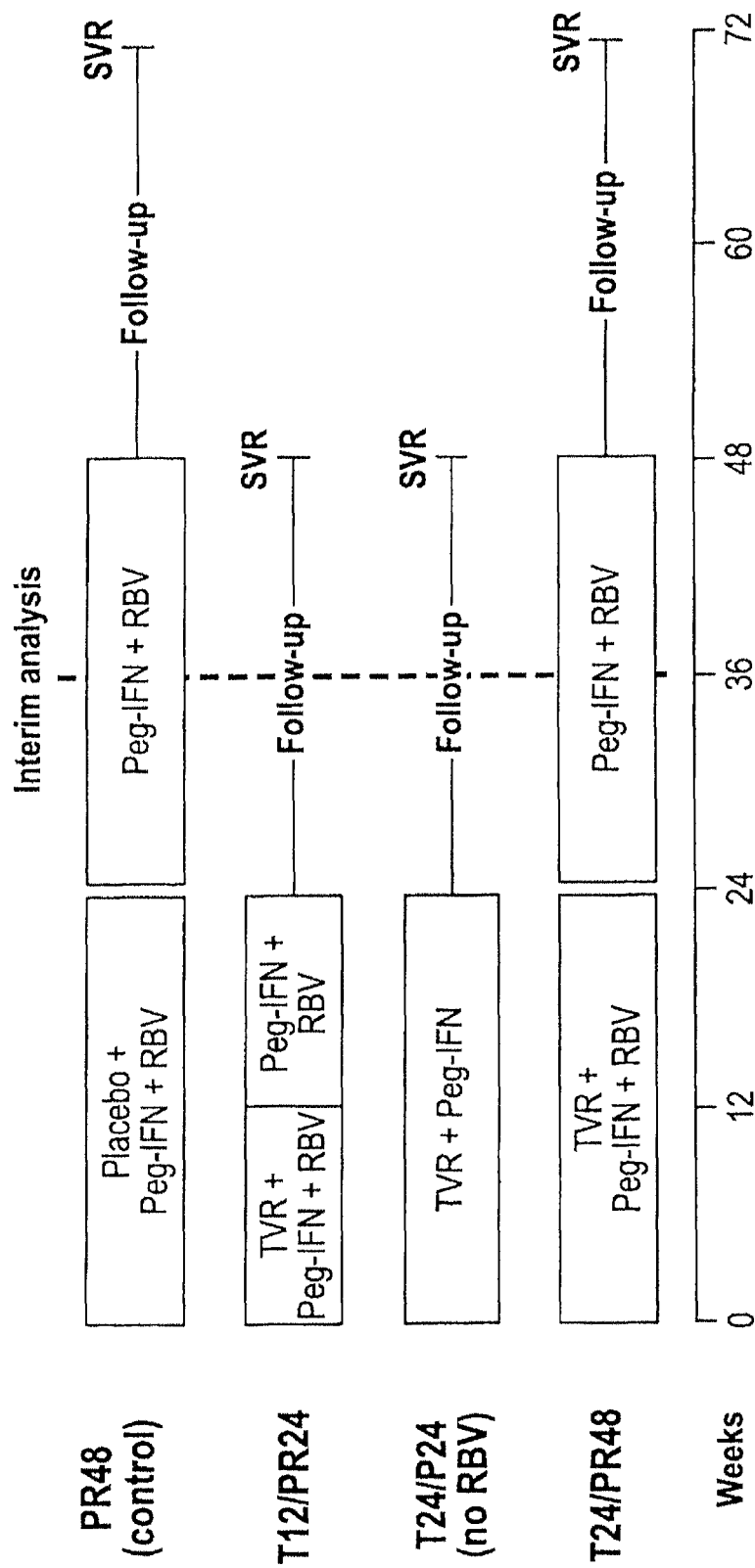
FIG. 1 depicts the PROVE3 study design.
Figure 2:
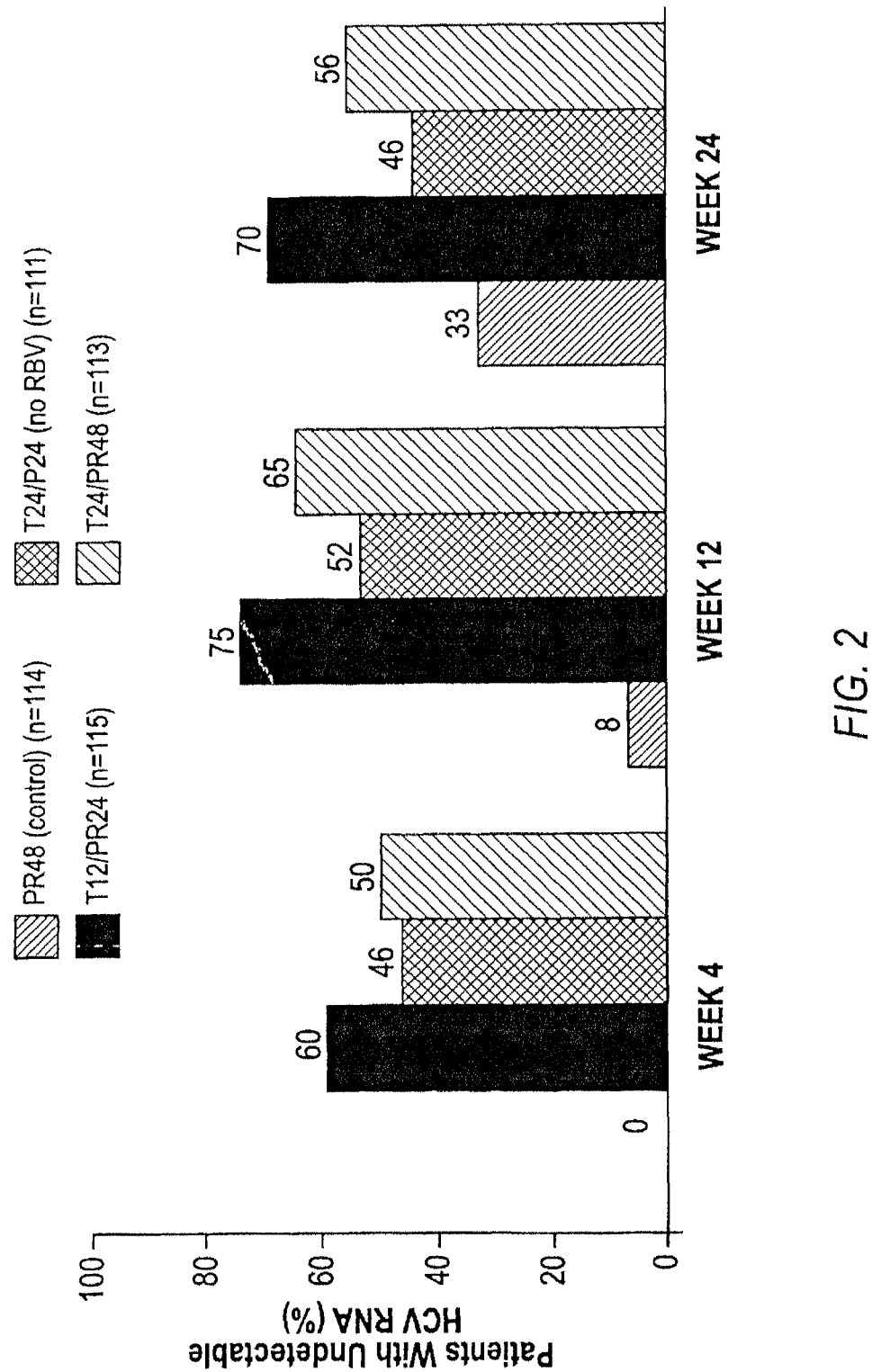
FIG. 2 depicts undetectable HCV at weeks 4, 12 and 24 by ITT analysis.
Figure 3:
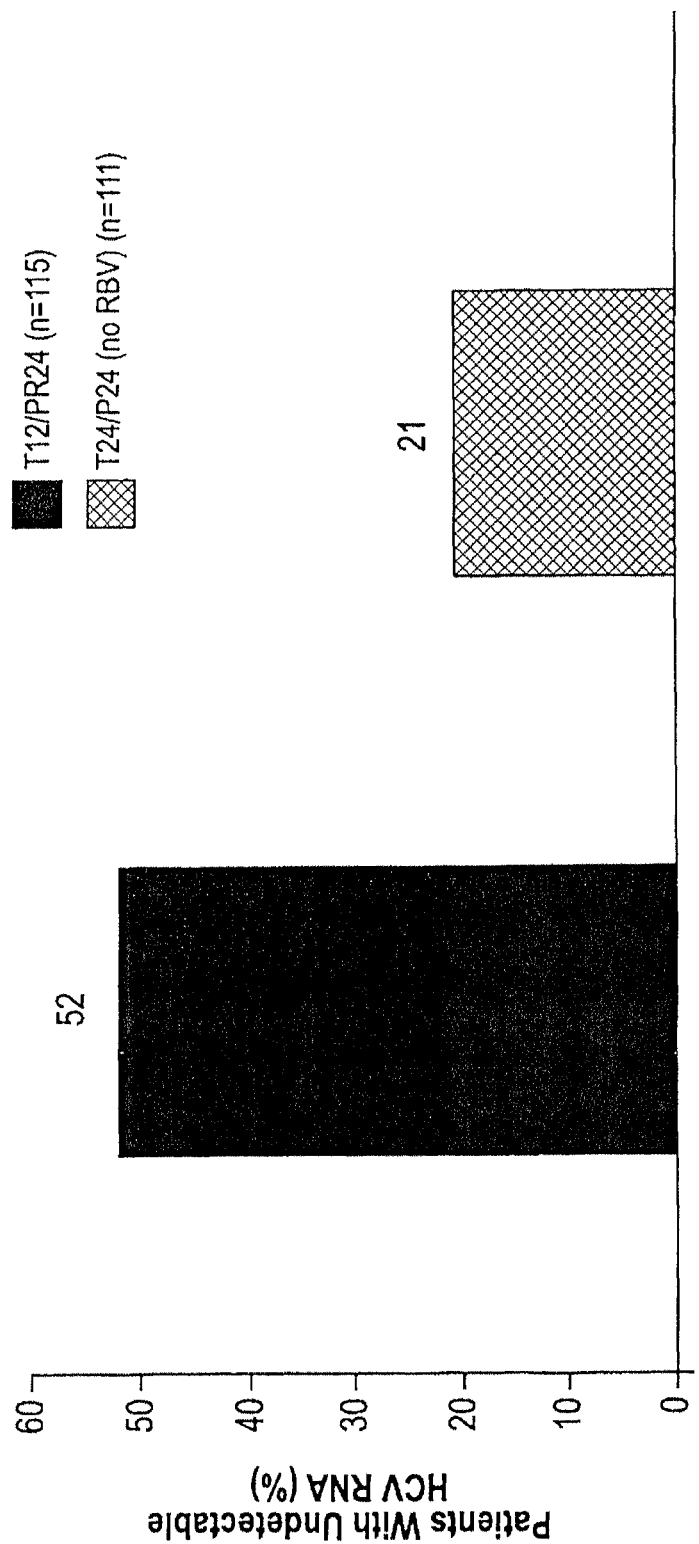
FIG. 3 depicts undetectable HCV at 12 weeks post-treatment by ITT analysis.
Figure 4:
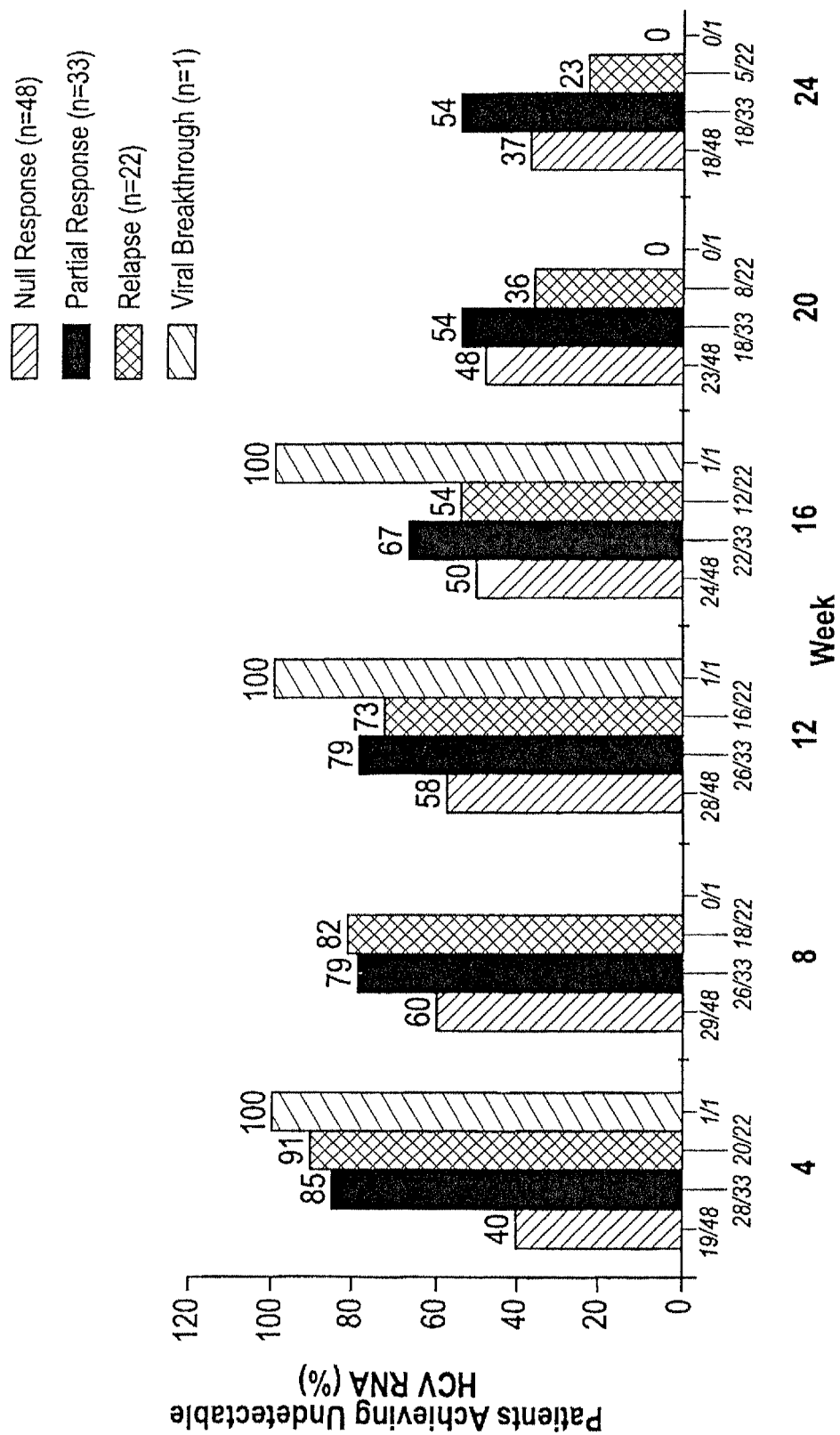
FIG. 4 depicts undetectable HCV RNA at Weeks 4, 8, 12, 16, 20 and 24 by Prior PR Virologic Response (ITT analysis).
Figure 5:
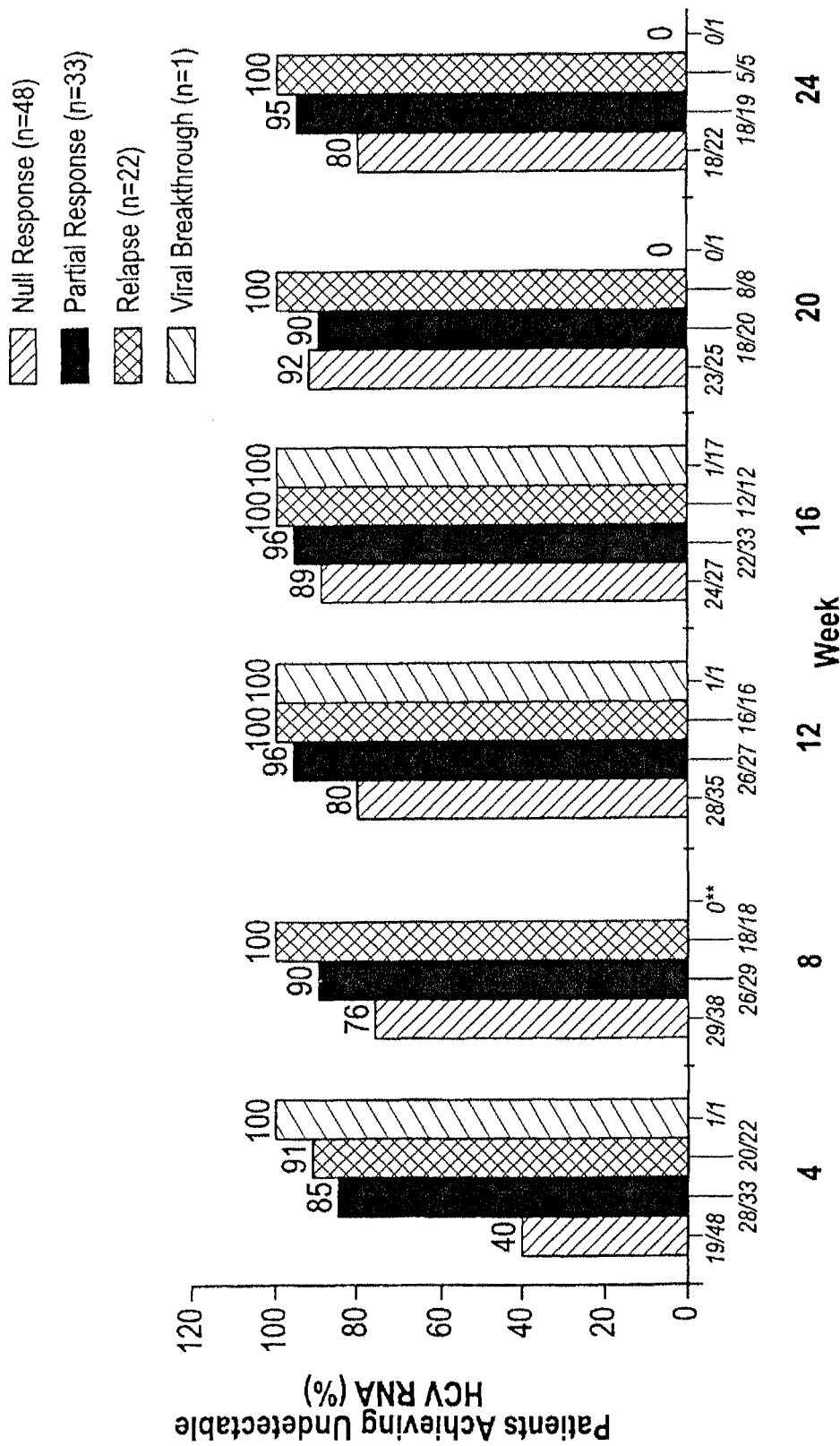
FIG. 5 depicts undetectable HCV RNA at Weeks 4, 8, 12, 16, 20 and 24 by Prior PR Virologic Response (as treated analysis).
Figure 6:
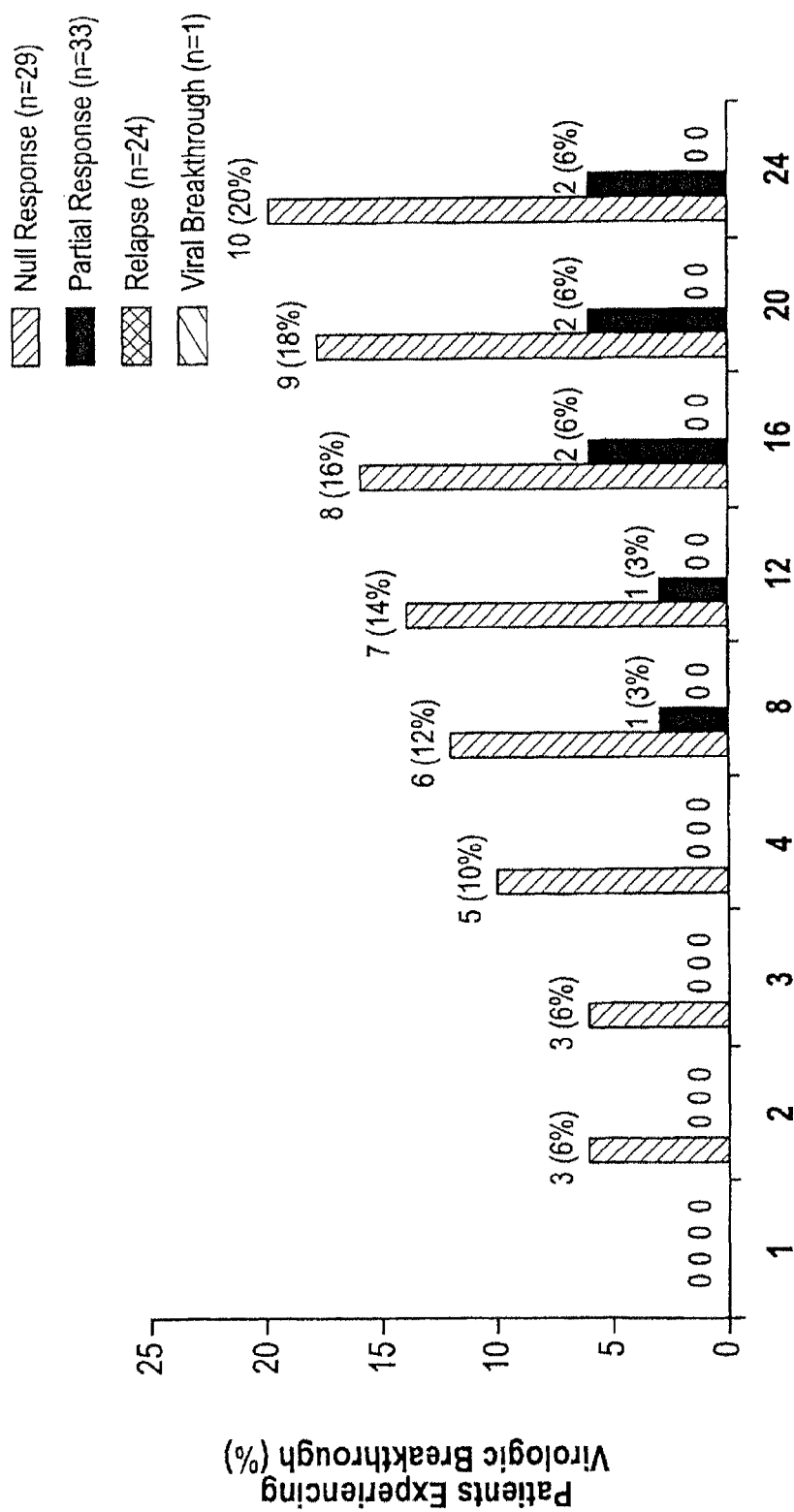
FIG. 6 depicts cumulative virologic breakthrough following T/PR treatment.
Figure 7:
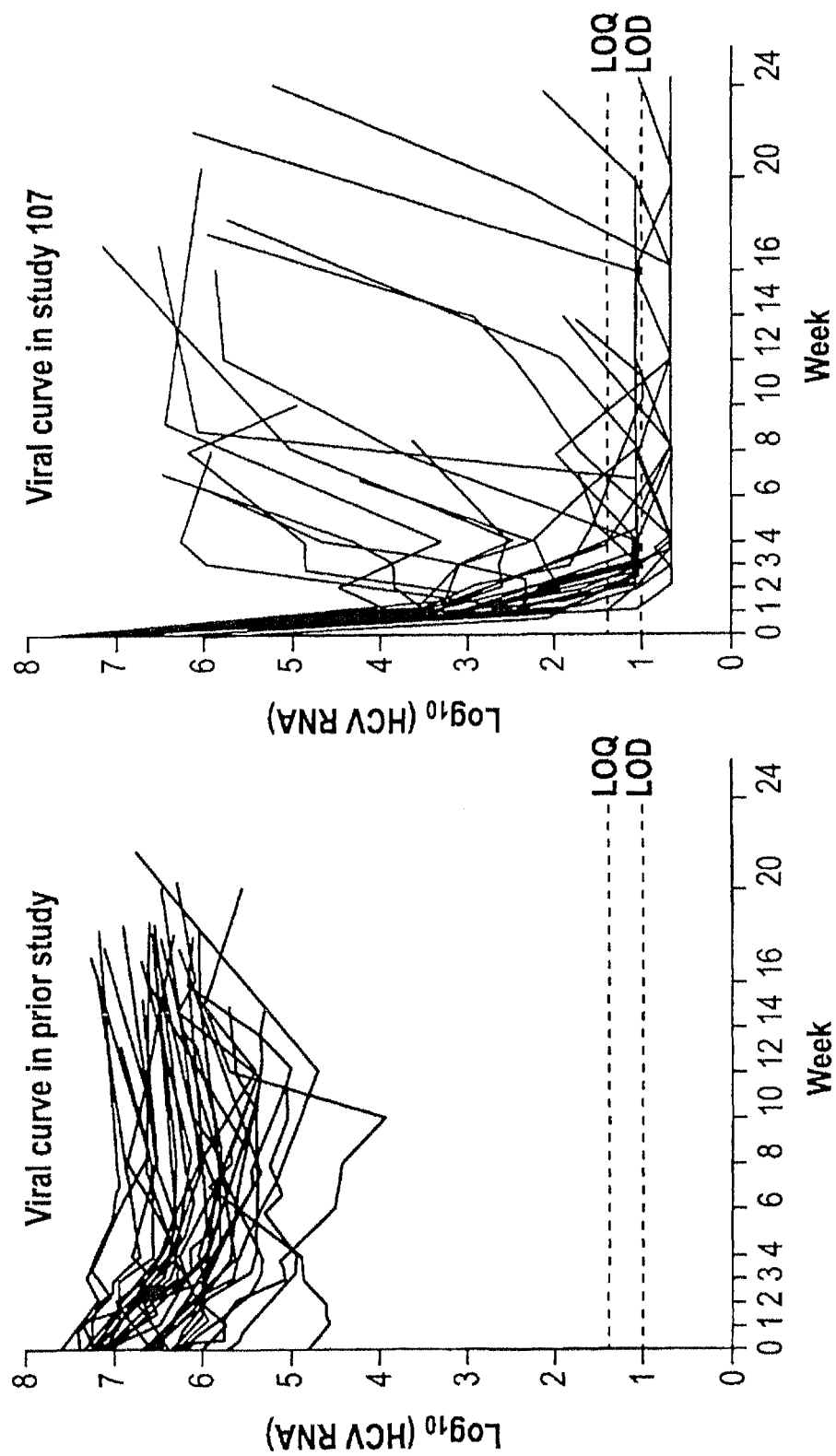
FIG. 7 depicts viral curves through week 24, prior null responders. LOQ=limit of quantification; LOD=limit of Detection.
Figure 8:
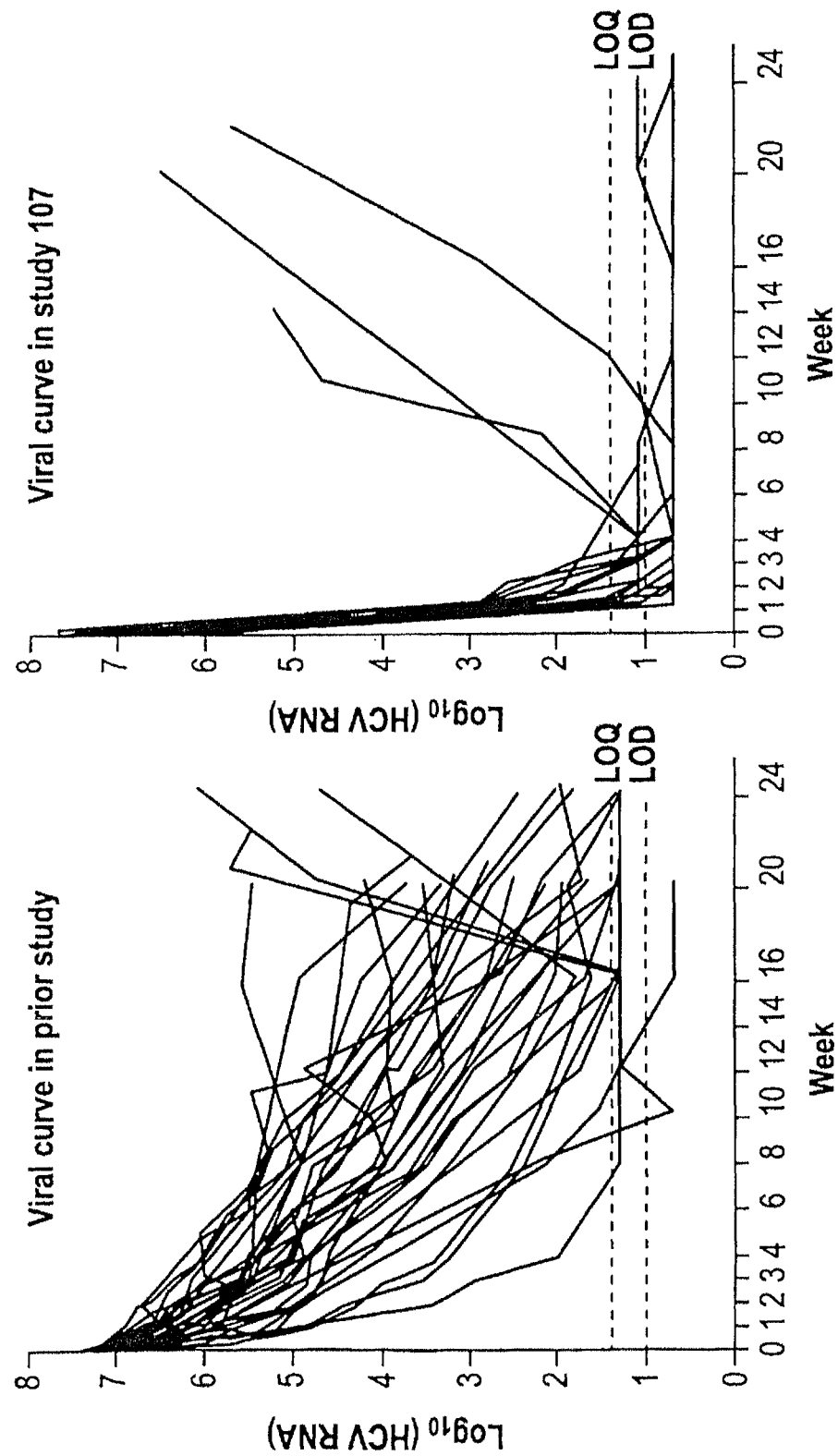
FIG. 8 depicts viral curves through week 24, prior partial responders. LOQ=limit of quantification; LOD=limit of Detection.
Figure 9:
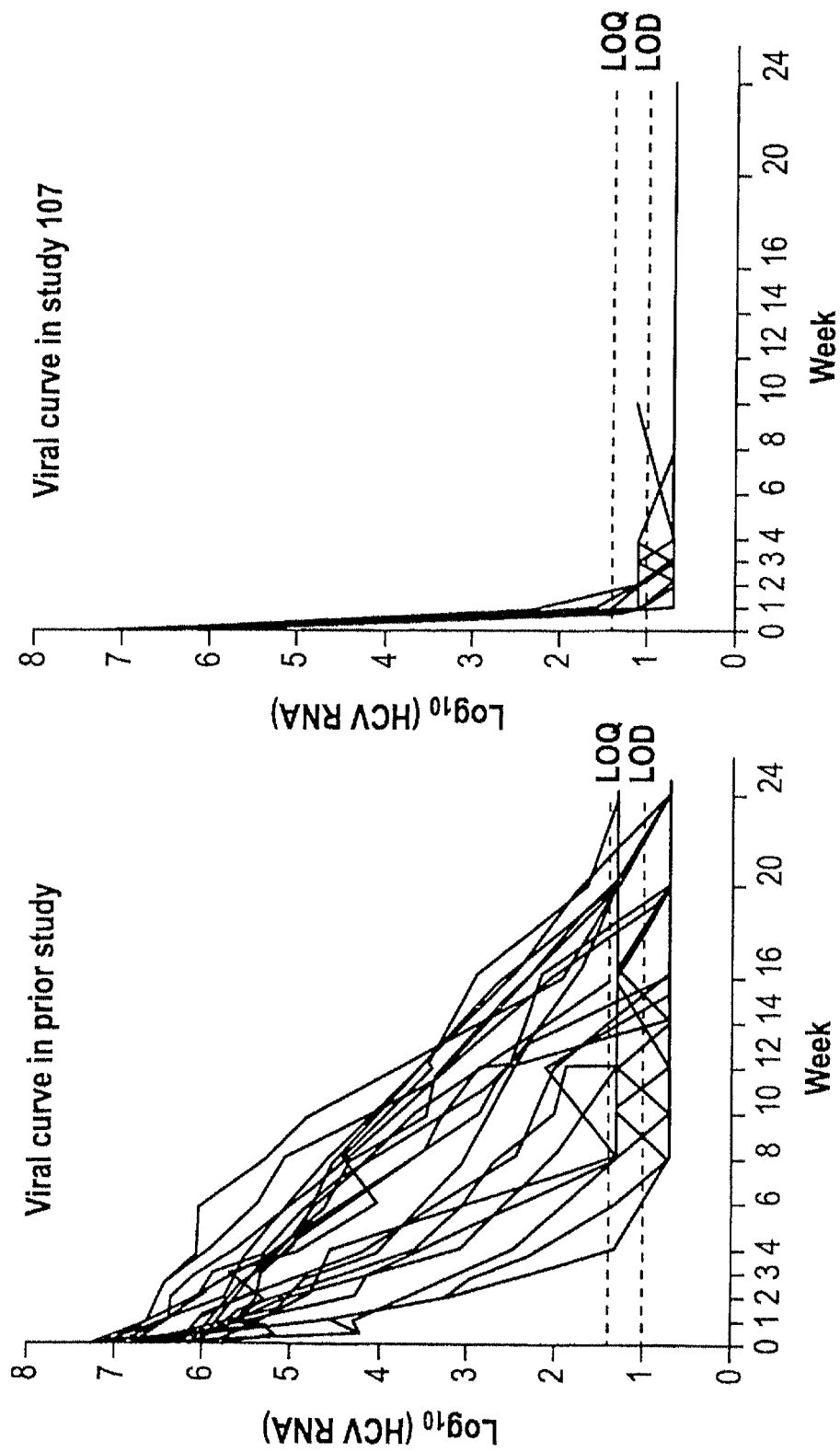
FIG. 9 depicts viral curves through week 24, prior relapsers. LOQ=limit of quantification; LOD=limit of Detection.
Figure 10:
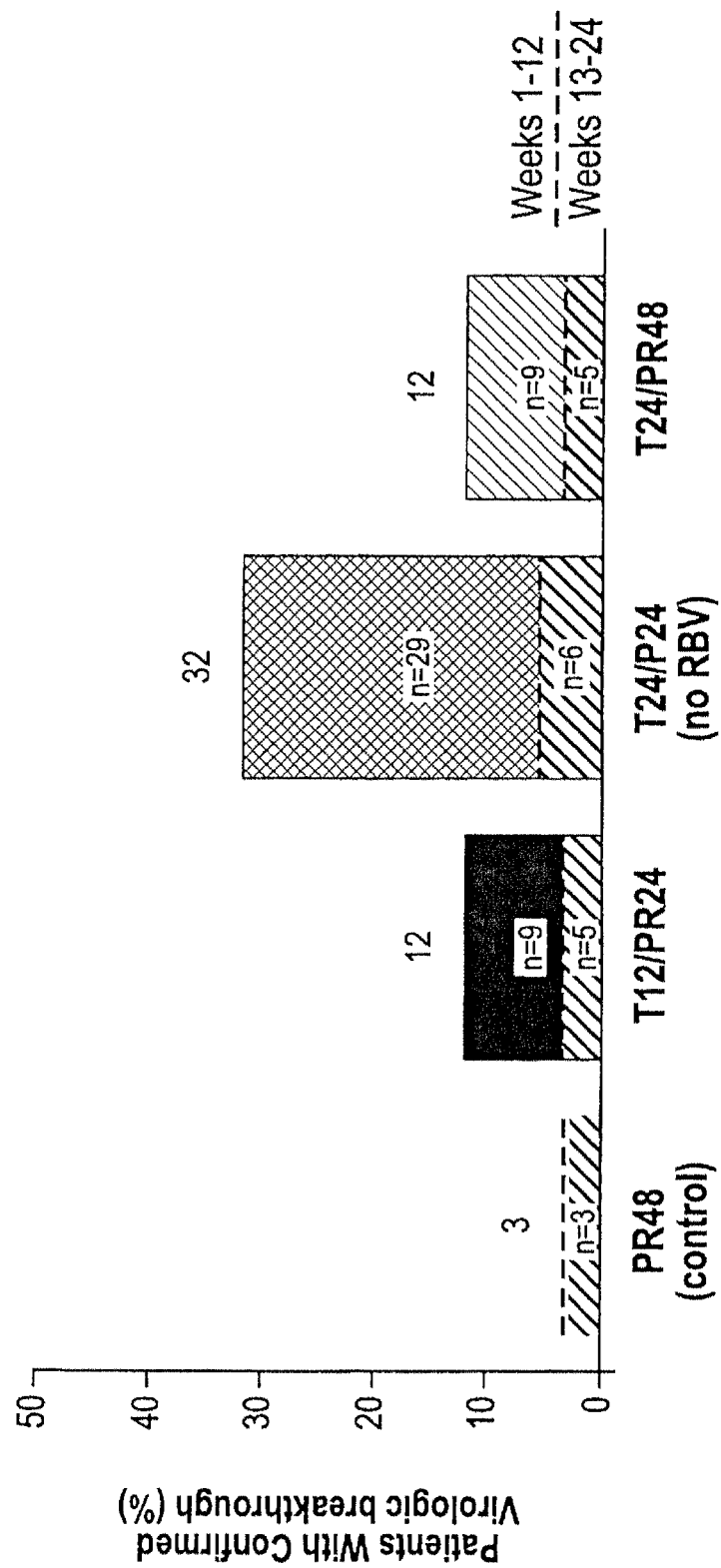
FIG. 10 depicts virologic breakthrough to week 24 of treatment.
Figure 11:
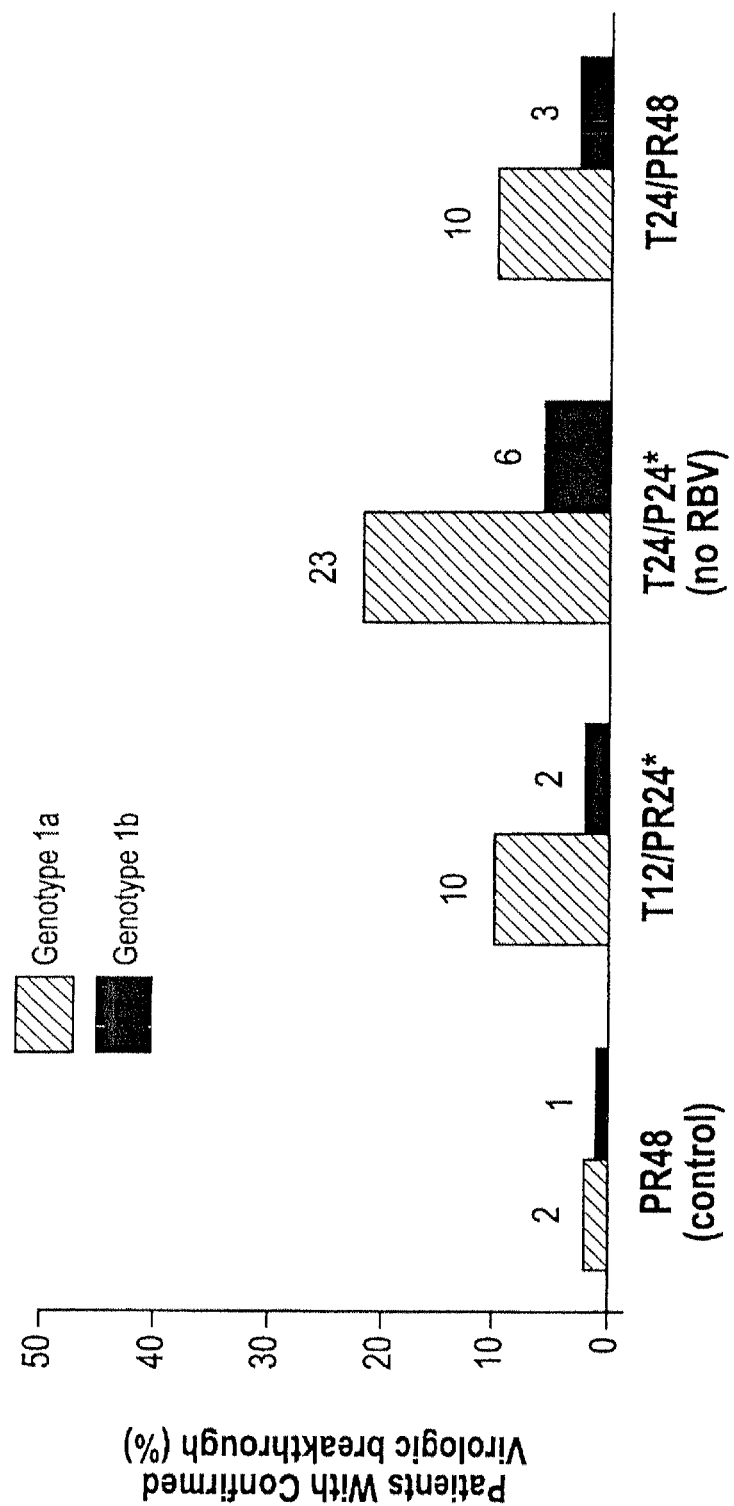
FIG. 11 depicts virologic breakthrough by genotype 1a and 1b.
Figure 12:
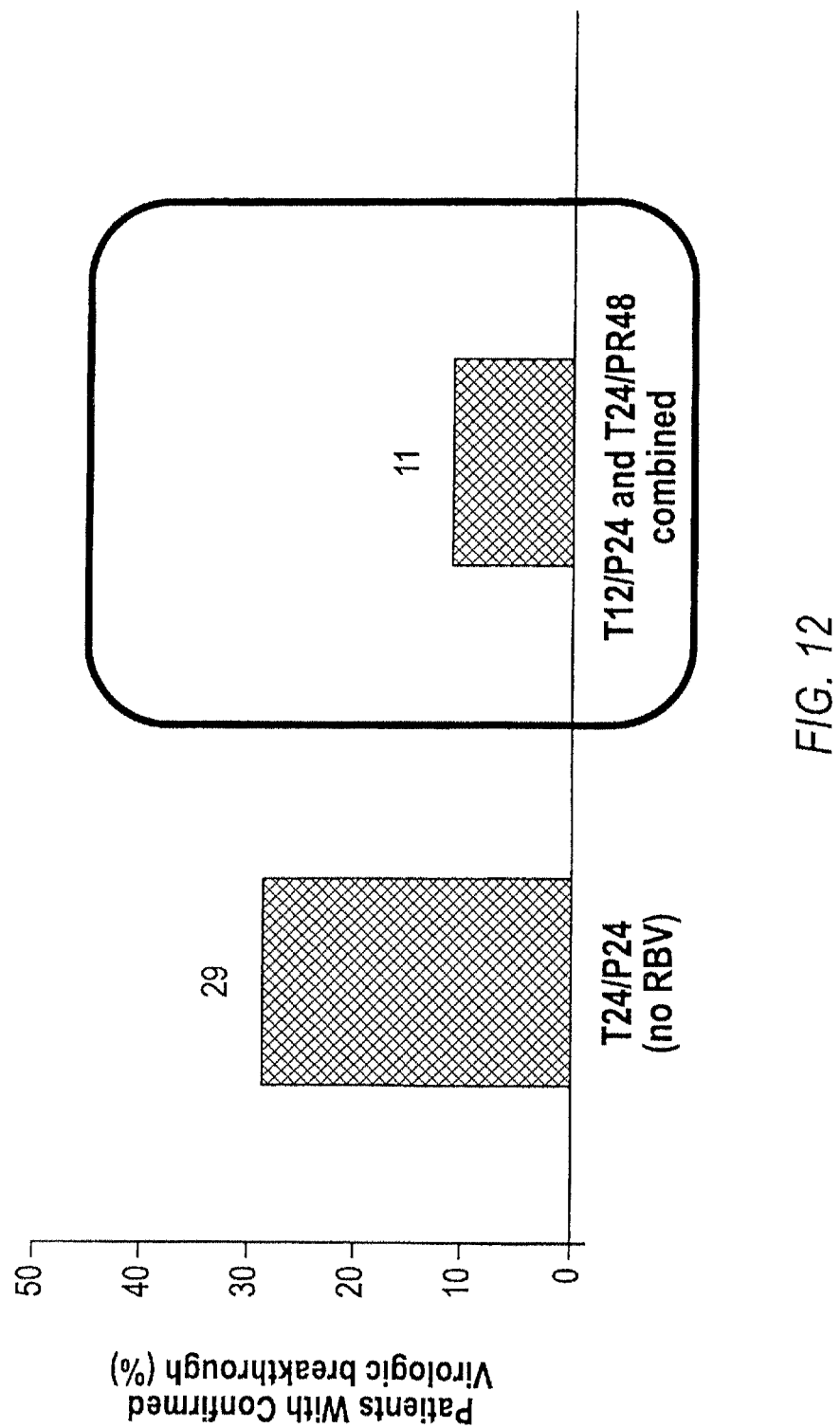
FIG. 12 depicts virologic breakthrough at week 24.

VX-950 is described in PCT Publication Numbers WO 02/018369, WO 2006/050250 and WO/2008/144072, with reference to the following structural formula, or a pharmaceutically acceptable salt thereof:

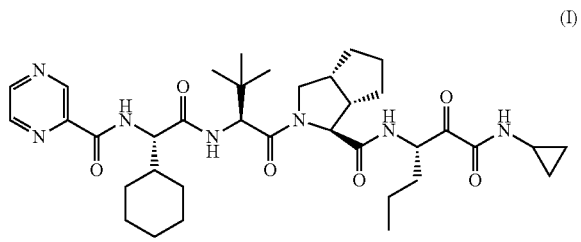 [SMILES: CCC[C@H](NC(=O)[C@@H]1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1]

(I)

Other descriptions of VX-950 can be found in PCT Publication Numbers WO 07/098,270 and WO 08/106,151.

Accordingly, one embodiment of this invention provides a therapeutic regimen comprising administering to a P/R non-responsive patient VX-950, or a pharmaceutically acceptable salt thereof,
in an amount of about 100 mg to about 1500 mg;
in an amount of about 300 mg to about 1500 mg;
in an amount of about 300 mg to about 1250 mg;
in an amount of about 450 mg;
in an amount of about 750 mg; or
in an amount of about 1250 mg;
wherein the amount is administered once, twice, or three times per day. A therapeutic regimen according to this invention is intended to include the administration of VX-950 in one or more dosage forms.

Another embodiment of this invention provides a method for treating or preventing a HCV infection in a P/R non-responsive patient comprising administering to the patient VX-950, or a pharmaceutically acceptable salt thereof, in an amount of about 1125 mg.

Another embodiment of this invention provides a method for treating or preventing a HCV infection in a P/R non-responsive patient comprising administering to the patient VX-950, or a pharmaceutically acceptable salt thereof, in an amount of about 300 mg to about 1500 mg.

In certain embodiments, the dose of VX-950 is at least about 300 mg. In other embodiments, the dose of VX-950 is at least about 450 mg. In other embodiments, the dose of VX-950 is at least about 500 mg. In other embodiments, the dose of VX-950 is at least about 750 mg. In other embodiments, the dose of VX-950 is at least about 1250 mg. In other embodiments, the dose of VX-950 is at least about 1500 mg.

In yet other embodiments, the dose of VX-950 is no more than about 1500 mg. In other embodiments, the dose of VX-950 is no more than about 1250 mg. In other embodiments, the dose of VX-950 is no more than about 750 mg. In other embodiments, the dose of VX-950 is no more than about 450 mg. In other embodiments, the dose of VX-950 is no more than about 500 mg. In other embodiments, the dose of VX-950 is no more than about 300 mg.

It should be understood that these lower and upper amounts may be combined to provide preferred dose ranges for administering VX-950. For example, in one embodiment, the VX-950, or the pharmaceutically acceptable salt thereof, is in an amount of about 300 mg to about 1250 mg.

In certain embodiments, VX-950 is administered in an amount of about 450 mg. VX-950 is administered in an amount of about 500 mg. In other embodiments, VX-950 is administered in an amount of about 600 mg. In other embodiments, VX-950 is administered in an amount of about 750 mg. In other embodiments, VX-950 is administered in an amount of about 1000 mg. In yet other embodiments, VX-950 is administered in an amount of about 1250 mg.

In any of these embodiments, the amount of VX-950 is administered once a day. Alternatively, the amount of VX-950 is administered twice a day (e.g., BID; q12h). Alternatively, the amount of VX-950 is administered three-times per day (e.g., TID; q8h). VX-950 may be administered with or without food.

VX-950 has also been tested in humans and found to be effective at inhibiting HCV replication. Applicants have demonstrated that administration of VX-950 was able to substantially decrease HCV RNA levels. Importantly, applicants have demonstrated that administration of VX-950 to subjects infected with HCV can inhibit the virus such that the viral RNA becomes undetectable using the Roche COBAS TAQ-MAN™ HCV/HPS assay (available from Roche Molecular Diagnostics). Of the 8 subjects receiving 750 mg of VX-950 every 8 hours (q8h), 4 had HCV RNA levels below the limit of quantitation (LLQ 30 IU/mL) and 2 of those 4 subjects had HCV RNA levels below the limit of detection (LLD 10 IU/mL).

Subjects receiving 750 mg of VX-950 every eight hours achieved a median reduction in HCV-RNA of greater than 4 $\log_{10}$ (i.e., 10,000-fold decrease) at the end of 14 days of treatment. A median reduction of HCV-RNA of greater than 2 $\log_{10}$ was seen in each of the other two VX-950 dose groups at the end of 14 days of treatment. Every subject receiving VX-950 achieved greater than a 2 $\log_{10}$ reduction in HCV-RNA within the first three days of treatment, and 26 of the 28 subjects receiving VX-950 had a 3 logic reduction in HCV-RNA within the first three days of treatment. See, Example 5.

It was demonstrated that plasma viral loads decline rapidly in patients treated with VX-950. Additionally, it was demonstrated that there was a slow return towards baseline HCV RNA levels after the end of dosing. Specifically, the rate of return to HCV RNA baseline levels following the end of treatment was slower than the rate of decline of HCV RNA upon treatment. These results together with achieving undetectable HCV RNA levels, indicate the effectiveness of VX-950 as a monotherapy.

Accordingly, this invention provides a method for treating a P/R non-responsive patient infected with HCV, comprising administering to the patient VX-950, or a pharmaceutically acceptable salt thereof, in an amount of: a) about 450 mg, 3 times per day, every 8 hours; b) about 750 mg, 3 times per day, every 8 hours; c) about 1250 mg, 2 times per day, every 12 hours; or d) about 1250 mg, 3 times per day, every 8 hours.

In other embodiments, this invention provides a method for treating a P/R non-responsive patient infected with HCV, comprising administering to the patient VX-950, or a pharmaceutically acceptable salt thereof, in an amount of about 1125 mg, two times per day; or in an amount of about 1125 mg, every 12 hours.

In other embodiments, this invention provides a method for administering VX-950 to a P/R non-responsive patient infected with HCV, such that the level of HCV RNA in the patient is at least about 2 log (preferably at least about 4 log) lower after treatment than before treatment. In another embodiment, this invention provides a method for administering VX-950 to a P/R non-responsive patient infected with HCV, such that the level of viral RNA in the patient is decreased to undetectable levels and remains at undetectable levels until a "sustained viral response" is achieved.

As used herein, "sustained viral response" or "SVR" means that after dosing is completed, viral RNA levels remain undetectable. "SVR12" means that 12 weeks after dosing is completed, viral RNA levels remain undetectable. "SVR24" means that 24 weeks after dosing is completed, viral RNA levels remain undetectable.

Without being bound by theory, it is thought that a method of this invention that employs 750 mg of VX 950 every 8 hours is preferred because the method results in higher trough levels. The trough level is the concentration that a drug drops down to in plasma just before next dose (i.e., the minimum concentration between doses). It is important, particularly in viral diseases, to maintain drug levels above a certain concentration to maintain appropriate inhibition of viral replication. Advantageously, applicants have found that one regimen, administering 750 mg of VX-950, every 8 hours, led to the highest trough levels of the tested regimens.

Accordingly, in a preferred embodiment, this invention provides a method comprising administering to a P/R non-responsive patient VX-950, or a pharmaceutically acceptable salt thereof, in an amount of about 750 mg, 3 times per day, every 8 hours.

As would be recognized, it advantageous to have flexible dosing schedules. Accordingly, in another embodiment of this invention, the administration is 3 times per day, but not every 8 hours, optionally with meals. In certain embodiments, VX-950 is administered with food.

This invention also provides a method for providing VX-950 to a P/R non-responsive human in need thereof, comprising administration to the human an oral dose of a composition comprising VX-950, wherein said dose provides to said human an average plasma concentration ($C_{avg}$) of VX-950 of at least about 750 ng/mL after the administration. In certain embodiments, the ($C_{avg}$) is about 1000 ng/mL or about 1250 ng/ml. In certain embodiments, said dose essentially contains 750 mg of VX-950. In these embodiments, the ($C_{avg}$) is obtained/attained within 3 hours after administration, preferably 2 hours, more preferably 1 hour after administering. In a preferred form of these embodiments, the ($C_{avg}$) is maintained over about 24 hours, and preferably over 12 weeks.

In certain embodiments, this invention provides a method for treating HCV infection in a P/R non-responsive patient by administering at least one dosage form comprising VX-950 over a 24 hour period, wherein the dosage form is administered to maintain a trough plasma VX-950 level minimum of about 750 ng/mL over the 24 hour period.

In certain forms of this embodiment, the dosage form is administered to maintain a trough plasma VX-950 level minimum of about 800 ng/mL, preferably about 900 ng/ml over the 24 hour period, and more preferably about 1000 ng/mL over the 24 hour period.

In certain preferred embodiments a therapeutically effective plasma concentration is obtained and a certain trough level is maintained. These methods are particularly useful for treating a human suffering from HCV infection by administering a VX-950 formulation, wherein the trough VX-950 plasma level is maintained at a minimum of about 750, 800, 900, or 1000 ng/mL over a 24 hour period. Without being bound by theory, trough levels of more than about 1500 ng/mL are thought to be not required by this invention. Accordingly, trough levels of about 750, 800, 900, 1000 ng/mL to about 1500 ng/mL (particularly 1000 to about 1500) are within the scope of this invention.

Also provided is a dosage form for delivering VX-950 to a P/R non-responsive human, wherein the dosage form comprises VX-950, said dosage form when administered at least once during a 24 hour period maintains a trough plasma VX-950 level that is at least about 750 ng/mL, 800 ng/mL, 900 ng/mL, or 1000 ng/mL over the 24 hour period to about 1500 ng/mL (particularly 1000 ng/mL to about 1500 ng/mL) over the 24 hour period.

Ideally, when a method of this invention involves treating a P/R non-responsive patient infected with HCV, the method involves achieving, relatively rapidly, a therapeutically effective plasma concentration of VX-950 and then maintaining the trough level such that an effective therapeutic response is achieved. An effective therapeutic response is, preferably, one or both of a) achieving a sustained viral response; and b) achieving undetectable HCV RNA in the plasma by at least 12 weeks (12 weeks or more). As used herein, HCV RNA being "undetectable" means that the HCV RNA is present in less than 10 IU/ml as determined by assays currently commercially available, and preferably as determined by the Roche COBAS TAQMAN™ HCV/HPS assay.

The relatively rapid drop in plasma concentration may be obtained by administering a loading dose to a patient. In one embodiment, the loading dose is about 1250 mg of VX-950.

In certain dosage forms of this invention, the dosage form (other than the dosage form used to administer the loading dose) contains about 750 mg of VX-950 and the dosage form is administered three times in each 24 hour period.

In certain embodiments, the treatment duration with VX-950 is shorter than the current standard of care.

In certain embodiments, VX-950 is administered for less than about 12 weeks (or less than 12 weeks).

In certain embodiments, VX-950 is administered for about 8-12 weeks (or 8-12 weeks).

In certain embodiments, VX-950 is administered for about 10 weeks (or 10 weeks).

Modeling data indicate that administration with VX-950 may eradicate wild-type virus within 10 weeks.

In certain embodiments, VX-950 is administered for less than about 10 weeks.

In certain embodiments, VX-950 is administered for about 2 weeks. Applicants have demonstrated that SVR was achieved in a patient receiving a 2 week treatment of VX-950.

In other embodiments, VX-950 is administered for less than about 8 weeks (or about 8 weeks or 8 weeks), less than about 6 weeks (or about 6 weeks or 6 weeks), or less than about 4 weeks (or about 4 weeks or 4 weeks).

In certain embodiments, a method according to this invention involves the treatment of a P/R non-responsive patient infected with genotype 1 Hepatitis C virus. Genotype 1 HCV infection is the most difficult strain of HCV to treat and the most prevalent strain in the United States.

Applicants have also demonstrated that administration of VX-950 decreases neopterin and ALT levels in vivo. AST (aspartate aminotransferase) levels were also decreased upon administration of VX-950. ALT is an enzyme that is present in liver cells; when liver cells are damaged or inflamed, ALT leaks from the cell into the blood. Blood ALT levels are useful as a marker of liver inflammation or damage.

Neopterin (6-d-erythro-trihydroxypropylpteridine) is a pteridine derivative that is produced during the metabolism of guanosine triphosphate (GTP). Neopterin is produced primarily by monocytes and macrophages upon activation by interferon gamma or interferon alfa and is a marker of inflammation. Neopterin levels are frequently elevated in chronic HCV infection. The expected plasma level of neopterin in healthy individuals is between 3.1 and 7.7 nmol/l.

Accordingly, applicants determined the changes in serum neopterin concentration as a marker of monocyte/macrophage activity during administration of an inhibitor of (HCV) NS3•4A protease. As described herein, VX-950 was administered for 14 days in a randomized, double blind, placebo controlled, multiple-dose study in 34 patients infected with HCV genotype 1 (Table 1). Patients received VX-950 450 mg q8h (n=10), 750 mg q8h (n=8), 1250 mg q12h (n=10), or placebo (n=6). Serum neopterin concentrations were measured by a quantitative competitive ELISA (ELltest® Neopterin, Brahms, Hennigsdorf, Germany) at pretreatment, at day 7 and 14, and at day 10 of follow-up. The lower limit of detection (LLD) was 2 nmol/l. HCV RNA was assessed at frequent intervals during the study by real-time PCR (CO-BAS® TAQMAN HCV Test; linear dynamic range of $3.0 \times 10^1$ to $2.0 \times 10^8$ HCV RNA IU/ml; LLD of 10 HCV RNA IU/ml; Roche Diagnostics, Branchburg, N.J.).

During administration of VX-950, every patient demonstrated a $>2-\log_{10}$ drop in viral load in all dose groups (Table 2). In the 750 mg q8h dose group, mean HCV RNA dropped $3.6 \log_{10}$ at day 3, and $4.3 \log_{10}$ at day 14. In the 450 mg q8h and 1250 mg q12h dose groups, maximal effect was seen at day 3 to day 7 followed by an increase in mean viral load between day 7 and day 14. Mean viral loads increased in all dose groups during follow-up. Advantageously, both HCV treatment naïve and previously treated patients benefit from the methods of this invention. Both prior-treated patients and treatment naïve patients responded to VX-950. For the avoidance of doubt, patients that may be treated according to the methods of this invention include those where HCV treatment has failed, including non-responding, rebound, relapse, and breakthrough patients.

Baseline neopterin was elevated in 23/34 patients (mean 9.33 nmol/l; upper limit of normal (ULN) 7.7 nmol/l). In the 750 mg dose group the decrease in neopterin compared to baseline and to placebo became significant at day 14 (750 mg q8h dose group baseline v day 14 10.48±0.84 nmol/l v 7.32±0.48 nmol/l P=0.0104, Mann Whitney test; 750 mg q8h dose group v placebo day 14 7.32±0.48 nmol/l v 9.81±1.36 nmol/l P=0.0036, unpaired two-tailed T test). Mean neopterin levels were within normal values at day 14 only in the 750 mg q8h dose group. In the 450 mg q8h dose group and the 1250 mg q12h dose group, decreases in mean neopterin levels were smaller. Mean neopterin levels did not change in the placebo group. Mean neopterin levels increased in all dose groups during follow-up.

Mean ALT levels, elevated at baseline, decreased during dosing in all groups. Mean ALT levels increased, returned toward baseline, in all dose groups during follow up.

Although HCV RNA increased in the 450 mg dose group and 1250 mg dose group after day 7, neopterin and especially ALT continued to decrease. Changes in mean neopterin concentration correlated with decline in HCV RNA and ALT levels during dosing of VX-950. Maximal decline in mean neopterin concentration was in the 750 mg q8h dose group at day 14. This was also the dose group with maximal reductions in HCV RNA at day 14. After day 7 in the 450 mg q8h and 1250 mg q12h dose groups, ALT and neopterin levels decreased while HCV RNA levels increased. These data suggest that inhibition of HCV replication by VX-950 results in a marked decline in systemic inflammatory activity associated with viral infection.

VX-950 also ameliorates elevated ALT levels in an animal model (see WO 2005/025517). Specifically, expression of WT-HCV protease-SEAP in SCID mice results in elevated ALT levels that can be ameliorated by treatment with VX-950. Expression of WT-HCV protease alone in SCID mice also results in time and dose dependent elevation of ALT levels.

Accordingly, another embodiment of this invention provides methods for treating or preventing one or more of liver damage, liver inflammation, steatosis, fatty liver, NAFLD, NASH, alcoholic steatosis, and Reye's syndrome in a P/R non-responsive patient that is either HCV positive or HCV negative. The invention also provides methods for hepatoprotection in a patient that is either HCV positive or negative.

Applicants have also demonstrated that VX-950 blocks immune evasion in vitro.

VX-950 restores IFNβ dependent gene expression in Sendai virus infected Huh7 cells. IFNβ promoter activity decreases in response to Sendai virus stimulation in the presence of WT HCVpro. VX-950 overcomes the WT HCVpro mediated suppression of IFNβ promoter activation.

Furthermore, NS3/4A is known to be involved in evasion of innate defenses, by e.g., TRIF-dependent mechanisms (as well as viral polyprotein processing). This immune evasion leads to viral persistence. Accordingly, a compound that inhibits both viral polyprotein processing and evasion of innate defenses is desirable. Advantageously, VX-950 has been shown to do both. In particular, VX-950 inhibits in vitro cleavage of TRIF, which is a TLR3 adaptor protein.

Without being bound by theory, modeling suggests that VX-950 inhibits TRIF cleavage by NS3 protease. TRIF binds to non-prime side of the NS3 protease active site. VX-950 binds to the same non-prime side of the active site as TRIF and blocks TRIF cleavage.

Additionally, applicants have shown that two VX-950 viral variants, A156T and A156V, show reduced ability to cleave either TRIF or 4A/4B. Because these viral variants are less fit, they are inefficient at both viral polyprotein processing and viral persistence. Without being bound by theory, this is related to steric hindrance of A156V affecting binding to 4A/4B & TRIF substrates.

This indicates that VX-950 acts as both a direct antiviral and as an inhibitor of immune evasion. Accordingly, this invention also provides methods of inhibiting HCV protease mediated evasion of host defenses.

These results together with the in vivo data disclosed herein indicate the effectiveness of VX-950 as a monotherapy.

The amounts of VX-950 according to this invention are administered in a single dosage form or in more than one dosage form. If in separate dosage forms, each dosage form is administered about simultaneously. For the avoidance of doubt, for dosing regimens calling for dosing more than once a day, one or more pill or dose may be given at each time per day (e.g., 1 pill, three times per day or 3 pills, three times per day). Most embodiments of this invention will employ at least 2 pills per dose).

VX-950 may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration. The D- and L-isomers at the N-propyl side chain of VX-950 are expressly included within this invention. Preferred embodiments of this invention employ VX-950.

As would be realized by skilled practitioners, if a method of this invention is being used to treat a patient prophylactically, and that patient becomes infected with Hepatitis C virus, the method may then treat the infection. Therefore, one embodiment of this invention provides methods for treating or preventing a Hepatitis C infection in a patient.

In addition to treating patients infected with Hepatitis C, the methods of this invention may be used to prevent a patient from becoming infected with Hepatitis C. Accordingly, one embodiment of this invention provides a method for preventing a Hepatitis C virus infection in a patient comprising administering to the patient a composition or dosage form according to this invention.

Methods of this invention may also involve administration of another component comprising an additional agent selected from an immunomodulatory agent; an antiviral agent; an inhibitor of HCV protease (other than VX-950); an inhibitor of another target in the HCV life cycle (other than NS3/4A protease); an inhibitor of internal ribosome entry, a broad-spectrum viral inhibitor; or a cytochrome P-450 inhibitor; or combinations thereof. The additional agent is also selected from an inhibitor of viral cellular entry.

Such anti-viral agents include, but are not limited to, immunomodulatory agents, such as α-, β-, and γ-interferons or thymosin, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase, polymerase, and metalloprotease inhibitors; inhibitors of internal ribosome entry; broad-spectrum viral inhibitors, such as IMPDH inhibitors (e.g., compounds described in U.S. Pat. Nos. 5,807,876, 6,498,178, 6,344,465, and 6,054,472; and PCT publications WO 97/40028, WO 98/40381, and WO 00/56331; and mycophenolic acid and derivatives thereof, and including, but not limited to, VX-497, VX-148, and VX-944); or any of their combinations.

Other agents (e.g., non-immunomodulatory or immunomodulatory compounds) may be used in combination with a compound of this invention include, but are not limited to, those specified in WO 02/18369, which is incorporated herein by reference (see, e.g., page 273, lines 9-22 and page 274, line 4 to page 276, line 11 this disclosure being specifically incorporated herein by reference).

Still other agents include those described in various published U.S. patent applications. These publications provide additional teachings of compounds and methods that could be used in combination with VX-950 in the methods of this invention, particularly for the treatment of hepatitis. It is contemplated that any such methods and compositions may be used in combination with the methods and compositions of the present invention. For brevity, the disclosure the disclosures from those publications is referred to be reference to the publication number but it should be noted that the disclosure of the compounds in particular is specifically incorporated herein by reference. Examples of such publications include U.S. Patent Application Publication Nos.: US 20040058982, US 20050192212, US 20050080005, US 20050062522, US 20050020503, US 20040229818, US 20040229817, US 20040224900, US 20040186125, US 20040171626, US 20040110747, US 20040072788, US 20040067901, US 20030191067, US 20030187018, US 20030186895, US 20030181363, US 20020147160, US 20040082574, US 20050192212, US 20050187192, US 20050187165, US 20050049220, and US 20050222236.

Still other agents include, but are not limited to, Albuferon™ (albumin-Interferon alpha) available from Human Genome Sciences; PEG-INTRON® (peginterferon alfa-2b, available from Schering Corporation, Kenilworth, N.J.); INTRON-A®, (VIRAFERON®, interferon alfa-2b available from Schering Corporation, Kenilworth, N.J.); ribavirin (1-beta-D-ribofuranosyl-1H-1,2,4-triazole-3-carboxamide, available from ICN Pharmaceuticals, Inc., Costa Mesa, Calif.; described in the Merck Index, entry 8365, Twelfth Edition); REBETROL® (Schering Corporation, Kenilworth, N.J.); COPEGUS® (Hoffmann-La Roche, Nutley, N.J.); PEGASYS® (peginterferon alfa-2a available Hoffmann-La Roche, Nutley, N.J.); ROFERON® (recombinant interferon alfa-2a available from Hoffmann-La Roche, Nutley, N.J.); BEREFOR® (interferon alfa 2 available from Boehringer Ingelheim Pharmaceutical, Inc., Ridgefield, Conn.); SUMIFERON® (a purified blend of natural alpha interferons such as Sumiferon available from Sumitomo, Japan); WELLFERON® (interferon alpha n1 available from Glaxo Wellcome Ltd., Great Britain); ALFERON® (a mixture of natural alpha interferons made by Interferon Sciences, and available from Purdue Frederick Co., CT); α-interferon; natural alpha interferon 2a; natural alpha interferon 2b; pegylated alpha interferon 2a or 2b; consensus alpha interferon (Amgen, Inc., Newbury Park, Calif.); REBETRON®(Schering Plough, Interferon-alpha 2B+Ribavirin); pegylated interferon alpha (Reddy, K. R. et al., "Efficacy and Safety of Pegylated (40-kd) Interferon alpha-2a Compared with Interferon alpha-2a in Noncirrhotic Patients with Chronic Hepatitis C," *Hepatology*, 33, 433-438 (2001); consensus interferon (INFERGEN®) (Kao, J. H., et al., "Efficacy of Consensus Interferon in the Treatment of Chronic Hepatitis," *J. Gastroenterol. Hepatol.*, 15, 1418-1423 (2000); lymphoblastoid or "natural" interferon; interferon tau (Clayette, P. et al., "IFN-tau, A New Interferon Type I with Antiretroviral activity" *Pathol. Biol.* (Paris) 47, 553-559 (1999); interleukin-2 (Davis, G. L. et al., "Future Options for the Management of Hepatitis C." *Seminars in Liver Disease*, 19, 103-112 (1999); Interleukin-6 (Davis et al., "Future Options for the Management of Hepatitis C," *Seminars in Liver Disease*, 19, 103-112 (1999); interleukin-12 (Davis, G. L. et al., "Future Options for the Management of Hepatitis C." *Seminars in Liver Disease*, 19, 103-112 (1999); and compounds that enhance the development of type 1 helper T cell response (Davis et al., "Future Options for the Management of Hepatitis C," *Seminars in Liver Disease*, 19, 103-112 (1999)). Also included are compounds that stimulate the synthesis of interferon in cells (Tazulakhova, E. B. et al., "Russian Experience in Screening, analysis, and Clinical Application of Novel Interferon Inducers" *J. Interferon Cytokine Res.*, 21 65-73) including, but are not limited to, double stranded RNA, alone or in combination with tobramycin, and Imiquimod (3M Pharmaceuticals; Sauder, D. N. "Immunomodulatory and Pharmacologic Properties of Imiquimod," *J. Am. Acad. Dermatol.*, 43 S6-11 (2000). See also, WO 02/18369, particularly page 272, line 15 to page 273, line 8, this disclosure being specifically incorporated herein by reference.

As is recognized by skilled practitioners, VX-950 is preferably administered orally. Interferon is not typically administered orally, although orally administered forms are in development. Nevertheless, nothing herein limits the methods or combinations of this invention to any specific dosage forms or regime. Thus, each component of a combination according to this invention may be administered separately, together, or in any combination thereof. As recognized by skilled practitioners, dosages of interferon are typically measured in IU (e.g., about 4 million IU to about 12 million IU). Interferon may also be dosed by micrograms. For example, a standard dose of Peg-Intron is 1.0-1.5 µg/kg/wk and of Pegasys is 180 µg/wk.

In some aspects, the method includes the administration of agents to a P/R non-responsive patient over two phases, an initial phase and a secondary phase. For instance the initial phase can be a period of less than about 12 or 24 weeks and the secondary phase can be greater or equal to about 12 weeks, e.g., the secondary phase can be between about 12-36 weeks. In certain embodiments, the secondary phase is 12 weeks. In still other embodiments, the secondary phase is 36 weeks. In certain embodiments, the sum of the initial and secondary phase is about 24 to 48 weeks (such as 24, 36, or 48 weeks). In some embodiments, the initial and secondary phases can be identical in duration.

VX-950 may be administered in either the initial, secondary, or both phases. In some embodiments, VX-950 is administered only in the initial phase. When VX-950 is administered only in the initial phase, VX-950 may be administered alone or in combination with other agents and one or more agents are administered in the secondary phase. The other agents can be one or more anti-viral agents, one or more other agents described herein, or combinations thereof. In some embodiments, the specific agents administered in the initial and secondary phases are identical.

In some embodiments, the method includes the administration of VX-950 for two weeks (initial phase) followed by 22 weeks of administration of a combination of Peginterferon alfa-2a (Peg-IFN) and ribavirin (RBV) (secondary phase). In other embodiments, the method includes the administration of VX-950 for two weeks (initial phase) followed by 46 weeks of administration of a combination of Peg-IFN and REV (secondary phase).

In still other embodiments, the method includes the administration of VX-950 for two weeks in combination with Peg-IFN (initial phase) followed by 22 weeks of administration of a combination of Peg-IFN and REV (secondary phase). In other embodiments, the method includes the administration of VX-950 for two weeks in combination with Peg-IFN (initial phase) followed by 46 weeks of administration of a combination of Peg-IFN and RBV (secondary phase), In still other embodiments, the method includes the administration of VX-950 for two weeks in combination with Peg-IFN and RBV (initial phase) followed by 22 weeks of administration of a combination of Peg-IFN and RBV (secondary phase). In other embodiments, the method includes the administration of VX-950 for two weeks in combination with Peg-IFN and REV (initial phase) followed by 46 weeks of administration of a combination of Peg-IFN and RBV (secondary phase).

In some embodiments, the method includes the administration of VX-950 for four weeks (initial phase) followed by 20 weeks of administration of a combination of Peginterferon alfa-2a (Peg-IFN) and ribavirin (RBV) (secondary phase). In other embodiments, the method includes the administration of VX-950 for four weeks (initial phase) followed by 44 weeks of administration of a combination of Peg-IFN and REV (secondary phase).

In still further embodiments, the method includes the administration of VX-950 for four weeks in combination with Peg-IFN (initial phase) followed by 20 weeks of administration of a combination of Peg-IFN and RBV (secondary phase). In other embodiments, the method includes the administration of VX-950 for four weeks in combination with Peg-IFN (initial phase) followed by 44 weeks of administration of a combination of Peg-IFN and REV (secondary phase).

In still other embodiments, the method includes the administration of VX-950 for four weeks in combination with Peg-IFN and RBV (initial phase) followed by 20 weeks of administration of a combination of Peg-IFN and REV (secondary phase). In other embodiments, the method includes the administration of VX-950 for four weeks in combination with Peg-IFN and REV (initial phase) followed by 44 weeks of administration of a combination of Peg-IFN and RBV (secondary phase).

In some embodiments, any of the initial phases described above can be conducted for about 12 weeks and the secondary phases can be conducted for about 12 weeks. Alternatively, the initial phase can be conducted for about 12 weeks and the secondary phase can be conducted for about 24 weeks. In still other aspects, the initial phase can be conducted for about 12 weeks and the secondary phase can be conducted for about 36 weeks.

In some embodiments, any of the initial phases described above can be conducted for about 8 weeks and the secondary phases can be conducted for about 16 weeks. Alternatively, the initial phase can be conducted for about 8 weeks and the secondary phase can be conducted for about 28 weeks. In still other aspects, the initial phase can be conducted for about 8 weeks and the secondary phase can be conducted for about 40 weeks.

In some embodiments, the method includes administering VX-950 in combination with Peg-IFN for less than 48 weeks. For instance, the method includes administering VX-950 in combination with Peg-IFN for less than 24 weeks.

In some embodiments, the method includes administering VX-950 in combination with Peg-IFN and RBV for less than 48 weeks. For instance, the method includes administering VX-950 in combination with Peg-IFN and RBV for less than 24 weeks.

In one embodiment, a method of this invention comprises administering to a P/R non-responsive patient VX-950 for about 2 weeks (or 2 weeks) followed by administering PEG-IFN and ribavirin for about 22 weeks (or 22 weeks) or about 46 weeks (or 46 weeks).

In some embodiments, the invention includes a therapeutic regimen comprising administering to a P/R non-responsive patient Peg-IFN and REV with VX-950 in an initial phase and administering Peg-IFN with RBV over a secondary phase, wherein the secondary phase occurs after the initial phase and VX-950 is administered in an amount of 750 mg every eight hours, peginterferon alfa 2a is administered in an amount of 180 mcg per week and ribavirin is administered in an amount of 1000 to 1200 mg per day.

In some embodiments, the invention includes a therapeutic regimen comprising administering to a P/R non-responsive patient Peg-IFN and RBV with VX-950 in an initial phase and administering Peg-IFN with RBV over a secondary phase, wherein the secondary phase occurs after the initial phase and VX-950 is administered in an amount of 750 mg every eight hours, peginterferon alfa 2b is administered in an amount of 1.5 mcg per kilogram per week and ribavirin is administered in an amount of 800 to 1200 mg per day.

In some embodiments, the invention includes a therapeutic regimen comprising administering to a P/R non-responsive patient Peg-IFN and RBV with VX-950 in an initial phase and administering Peg-IFN with RBV over a secondary phase, wherein the secondary phase occurs after the initial phase and VX-950 is administered in an amount of 1125 mg every twelve hours, peginterferon alfa 2a is administered in an amount of 180 mcg per week and ribavirin is administered in an amount of 1000 to 1200 mg per day.

In some embodiments, the invention includes a therapeutic regimen comprising administering to a P/R non-responsive patient Peg-IFN and RBV with VX-950 in an initial phase and administering Peg-IFN with RBV over a secondary phase, wherein the secondary phase occurs after the initial phase and VX-950 is administered in an amount of 750 mg every eight hours, peginterferon alfa 2b is administered in an amount of 1.5 mcg per kilogram per week and ribavirin is administered in an amount of 800 to 1200 mg per day.

Modeling data also indicate that VX-950 resistant variants, such as V36A/M, T54A, R155K/T, A156S A156V/T, V36A/M-R155K/T, and V36A/M-A156V/T, may be eradicated mainly by administering PEG-IFN and ribavirin for about 10-24 weeks (or 10-24 weeks) following VX-950 treatment. Certain of these regimens represent a reduction in treatment in the current standard of care treatment regimen lasting 24-48 weeks.

Accordingly, this invention also provides methods for administering VX-950 to a P/R non-responsive patient in combination with an interferon. In certain embodiments, the interferon is administered for about 10 weeks (or 10 weeks), about 12 weeks (or 12 weeks), about 14 weeks (or 14 weeks). Ribavirin is also optionally administered for all or part of the regimen, including but not limited to, the entire regimen.

In one embodiment, a method of this invention comprises administering a combination of VX-950 and Peg-IFN for about 12 weeks (or 12 weeks).

In one embodiment, a method of this invention comprises administering a combination of VX-950 and Peg-IFN for about 24 weeks (or 24 weeks).

For the avoidance of doubt, it should be understood that this invention includes, but is not limited to, a regimen involving administering VX-950 and an interferon for about 8 weeks (or 8 weeks) followed by administering interferon for about 16 weeks (or 16 weeks) for a total treatment regimen of about 24 weeks (or 24 weeks). Also provided is a regimen involving administering VX-950 and an interferon for about 12 weeks (or 12 weeks) followed by administering interferon for about 12 weeks (or 12 weeks) for a total treatment regimen of about 24 weeks (or 24 weeks). Such regimens optionally provide administration of ribavirin for all or part of the regimen, including but not limited to, the entire regimen of about 24 weeks (or 24 weeks).

In one embodiment, a method of this invention comprises administering a combination of VX-950, Peg-IFN, and ribavirin for about 12 weeks (or 12 weeks).

In one embodiment, a method of this invention comprises administering a combination of VX-950, Peg-IFN, and ribavirin for about 12 weeks (or 12 weeks) followed by administering Peg-IFN and ribavirin for about 12 weeks (or 12 weeks).

In one embodiment, a method of this invention comprises administering a combination of VX-950, Peg-IFN, and ribavirin for about 12 weeks (or 12 weeks) followed by administering Peg-IFN and ribavirin for about 36 weeks (or 36 weeks).

In one embodiment, a method of this invention comprises administering a combination of VX-950, Peg-IFN, and ribavirin for about 24 weeks (or 24 weeks) followed by administering PEG-IFN and ribavirin for about 24 weeks (or 24 weeks).

In one embodiment, the invention provides a therapeutic regimen comprising administering to a P/R non-responsive patient Peg-IFN and RBV with VX-950 in an initial phase and administering Peg-IFN with RBV over a secondary phase, wherein the secondary phase occurs after the initial phase and extends for a period of less than 48 weeks.

In one embodiment, the invention provides a therapeutic regimen, wherein the VX-950, or a pharmaceutically acceptable salt thereof, is administered in an amount of about 300 mg to about 1250 mg.

In one embodiment, the invention provides a therapeutic regimen, wherein the VX-950, or a pharmaceutically acceptable salt thereof, is administer in an amount of about 450 mg.

In one embodiment, the invention provides a therapeutic regimen, wherein the VX-950, or a pharmaceutically acceptable salt thereof, is administer in an amount of about 750 mg.

In one embodiment, the invention provides a therapeutic regimen, wherein the VX-950, or a pharmaceutically acceptable salt thereof, is administer in an amount of about 1250 mg.

In one embodiment, the invention provides a therapeutic regimen, wherein the amount is administered once per day.

In one embodiment, the invention provides a therapeutic regimen, wherein the amount is administered twice per day.

In one embodiment, the invention provides a therapeutic regimen, wherein the amount is administered three times per day.

In one embodiment, the invention provides a therapeutic regimen, wherein the amount is administered every 24 hours.

In one embodiment, the invention provides a therapeutic regimen, wherein the amount is administered every 12 hours.

In one embodiment, the invention provides a therapeutic regimen, wherein the amount is administered every 8 hours.

In some embodiments, the secondary phase extends for a period of less than 24 weeks.

In some embodiments, the secondary phase extends for a period of about 12 weeks.

In some embodiments, the initial phase extends for a period of less than 24 weeks.

In some embodiments, the initial phase extends for a period of about 12 weeks.

In some embodiments, the P/R non-responsive patient is a week 4 null responder.

In some embodiments, the P/R non-responsive patient is a week 12 null responder.

In one embodiment, SVR12 is achieved in greater than 40% of null responders.

In some embodiments, the P/R non-responsive patient is a partial responder.

In one embodiment, SVR12 is achieved in greater than 40% of partial responders.

In some embodiments, the P/R non-responsive patient is a breakthrough responder.

In one embodiment, SVR12 is achieved in greater than 40% of breakthrough responders.

In some embodiments, the P/R non-responsive patient is a relapser responder.

In one embodiment, SVR12 is achieved in greater than 35% of relapser responders.

In other embodiments, SVR12 is achieved in 36% of relapser responders.

A cytochrome P450 monooxygenase ("CYP") inhibitor used in connection with this invention is expected to inhibit metabolism of VX-950. Therefore, the cytochrome P450 monooxygenase inhibitor would be in an amount effective to inhibit metabolism of VX-950. Accordingly, the CYP inhibitor is administered to a P/R non-responsive patient in an amount such that the bioavailability of or exposure to VX-950 is increased in comparison to VX-950 in the absence of the CYP inhibitor. CYP inhibitors include, but are not limited to, ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole.

Methods for measuring the ability of a compound to inhibit cytochrome P50 monooxygenase activity are known (see, U.S. Pat. No. 6,037,157). Methods for evaluating the influence of co-administration of VX-950 and a CYP inhibitor in a subject are also known (US2004/0028755). Any such methods could be used in connection with this invention to determine the pharmacokinetic impact of a combination.

One embodiment of this invention provides a method for administering an inhibitor of CYP3A4 and VX-950 to a P/R non-responsive patient.

The methods herein may involve administration or co-administration to a P/R non-responsive patient of a) combinations of VX-950 and another agent; or b) VX-950 in more than one dosage form. Co-administration includes administering each inhibitor in the same dosage form or in different dosage forms. When administered in different dosage forms, the inhibitors may be administered at different times, including about simultaneously or in any time period around administration of the other dosage forms. Separate dosage forms may be administered in any order. That is, any dosage forms may be administered prior to, together with, or following the other dosage forms.

VX-950, and any additional agent, may be formulated in separate dosage forms. Alternatively, to decrease the number of dosage foams administered to a patient, VX-950, and any additional agent, may be formulated together in any combination. Any separate dosage forms may be administered at the same time or different times. It should be understood that dosage forms should be administered within a time period such that the biological effects were advantageous.

According to the regimens and dosage forms of this invention, VX-950 is present in an amount effective to decrease the viral load in a sample or in a patient, wherein said virus encodes a NS3/4A serine protease necessary for the viral life cycle (or in an amount effective to carry out a method of this invention), and a pharmaceutically acceptable carrier. Alternatively, a composition of this invention comprises an additional agent as described herein. Each component may be present in individual compositions, combination compositions, or in a single composition.

If pharmaceutically acceptable salts of compounds are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, particularly a human being.

Such pharmaceutical compositions of the present invention (as well as compositions for use in methods, combinations, kits, and packs of this inventions) may be administered orally, parenterally, sublingually, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously. More preferably, the compositions are administered orally.

Sterile injectable forms of the compositions of and according to this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage foams including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In compositions of this invention comprising VX-950 and an additional agent, VX-950 and the additional agent should be present at dosage levels of between about 10 to 100%, and more preferably between about 10 to 80% of the dosage normally administered in a monotherapy regimen.

The pharmaceutical compositions of this invention may be orally administered in any orally acceptable dosage form including, but not limited to, capsules, tablets, pills, powders, granules, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. Acceptable liquid dosage forms include emulsions, solutions, suspensions, syrups, and elixirs.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

As is recognized in the art, pharmaceutical compositions may also be administered in the form of liposomes.

Applicants have demonstrated that VX-950 is orally bioavailable. Accordingly, preferred pharmaceutical compositions of this invention are formulated for oral administration.

For the CYP inhibitor, the dosage levels of between about 0.001 to about 200 mg/kg body weight per day, would be typical. More typical would be dosage levels of between about 0.1 to about 50 mg/kg or about 1.1 to about 25 mg/kg per day.

For preferred dosage forms of ritonavir, see U.S. Pat. No. 6,037,157, and the documents cited therein: U.S. Pat. Nos. 5,484,801, 5,948,436 and International Applications WO 95/07696 and WO 95/09614.

Administrations in connection with this invention can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, the judgment of the treating physician and the severity of the particular disease being treated, prior treatment history, co-morbidities or concomitant medications, baseline viral load, race, duration of diseases, status of liver function and degree of liver fibrosis/cirrhosis, and the goal of therapy (eliminating circulating virus per-transplant or viral eradication). The amount of active ingredients will also depend upon the particular described compound and the presence or absence and the nature of the additional anti-viral agent in the composition.

According to another embodiment, the invention provides a method for treating a P/R non-responsive patient infected with a virus characterized by a virally encoded NS3/4A serine protease that is necessary for the life cycle of the virus by administering to said patient a pharmaceutically acceptable composition of this invention. Preferably, the methods of this invention are used to treat a patient suffering from a HCV infection. Such treatment may completely eradicate the viral infection or reduce the severity thereof. Preferably, the patient is a mammal. More preferably, the patient is a human being.

The dosages herein are preferably for use in vivo. Nevertheless, this is not intended as a limitation to using of these amounts of VX-950 for any purpose. In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

This invention also provides a process for preparing a composition comprising VX-950, or a pharmaceutically acceptable salt thereof, and a pharmaceutically acceptable carrier, adjuvant, or vehicle comprising the step of combining the VX-950, or the pharmaceutically acceptable salt thereof, and the pharmaceutically acceptable carrier, adjuvant, or vehicle, wherein the dosage of VX-950 in the composition is in accordance with any embodiment of this invention. An alternative embodiment of this invention provides a process wherein the composition comprises one or more additional agent as described herein.

This invention also provides therapeutic regimens comprising VX-950, or a pharmaceutically acceptable salt thereof, at the dosages disclosed herein. In an alternative embodiment of this invention, the therapeutic regimen further comprises one or more of additional agent as described herein.

Pharmaceutical compositions may also be prescribed to the patient in "patient packs" containing the whole course of treatment in a single package, usually a blister pack. Patient packs have an advantage over traditional prescriptions, where a pharmacist divides a patients supply of a pharmaceutical from a bulk supply, in that the patient always has access to the package insert contained in the patient pack, normally missing in traditional prescriptions. The inclusion of a package insert has been shown to improve patient compliance with the physician's instructions.

It will be understood that the administration of the combination of the invention by means of a single patient pack, or patient packs of each formulation, containing within a package insert instructing the patient to the correct use of the invention is a desirable additional feature of this invention.

According to a further aspect of the invention is a pack comprising at least VX-950 (in dosages according to this invention) and an information insert containing directions on the use of the combination of the invention. Any composition, dosage form, therapeutic regimen or other embodiment of this invention may be presented in a pharmaceutical pack. In an alternative embodiment of this invention, the pharmaceutical pack further comprises one or more of additional agent as described herein. The additional agent or agents may be provided in the same pack or in separate packs.

Another aspect of this involves a packaged kit for a patient to use in the treatment of HCV infection or in the prevention of HCV infection (or for use in another method of this invention), comprising: a single or a plurality of pharmaceutical formulation of each pharmaceutical component; a container housing the pharmaceutical formulation(s) during storage and prior to administration; and instructions for carrying out drug administration in a manner effective to treat or prevent HCV infection.

Accordingly, this invention provides kits for the simultaneous or sequential administration of a dose of VX-950 (and optionally an additional agent). Typically, such a kit will comprise, e.g. a composition of each compound and optional additional agent(s) in a pharmaceutically acceptable carrier (and in one or in a plurality of pharmaceutical formulations) and written instructions for the simultaneous or sequential administration.

In another embodiment, a packaged kit is provided that contains one or more dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

A kit according to this invention could embody any aspect of this invention such as any composition, dosage form, therapeutic regimen, or pharmaceutical pack.

The packs and kits according to this invention optionally comprise a plurality of compositions or dosage forms. Accordingly, included within this invention would be packs and kits containing one composition or more than one composition.

Although certain exemplary embodiments are depicted and described below, it will be appreciated that compounds of this invention can be prepared according to the methods described generally above using appropriate starting materials generally available to one of ordinary skill in the art.

As used herein "P/R non-responsive" includes patients who do not achieve or maintain a sustained virologic response (SVR) (undetectable HCV RNA 24 weeks after the completion of treatment) to the standard peg-IFN with RBV treatment, and patients who have had a lack of response. Lack of response is defined as a <2–log 10 decline from baseline in HCV RNA, as a failure to achieve undetectable levels of HCV virus, or as a relapse following discontinuation of treatment. As defined above, undetectable HCV RNA means that the HCV RNA is present in less than 10 IU/mL as determined by assays currently commercially available, for example, as determined by the Roche COBAS TagMan™ HCV/HPS assay. For example, "P/R non-responsive" includes "week 4 null responders", "week 12 null responders", "week 24 null responders", "week 26 to week 48 null responders", "partial responders", "viral breakthrough responders" and "relapser responders" with the standard peg-IFN with RBV treatment. A "week 4 null responder" is defined by a <1–log 10 drop in HCV RNA (not having a 1–log 10 decrease from baseline in HCV RNA) at week 4 of the standard peg-IFN with RBV treatment. A "week 12 null responder" is defined by a <2–log 10 drop in HCV RNA at week 12 (not having achieved an early viral response (EVR), a 2–log 10 decrease from the baseline in HCV RNA at week 12) of the standard peg-IFN with RBV treatment. A "week 24 null responder" is defined as a subject who has had detectable HCV RNA at week 24 of the standard peg-IFN with REV treatment. A "week 26 to week 48 null responder" is defined as a subject who had detectable HCV RNA between weeks 26 and 48 of the standard peg-IFN with REV treatment. A "partial responder" is defined by a ≥2–log 10 drop at week 12, but detectable HCV RNA at week 24 of the standard peg-IFN with RBV treatment. A "viral breakthrough responder" is defined by detectable HCV-RNA after achieving undetectable HCV-RNA during peg-IFN with RBV treatment. Viral breakthrough is defined as i) an increase in HCV RNA of >1–log 10 compared to the lowest recorded on-treatment value or ii) an HCV RNA level of >100 IU/ml, in a patient who had undetectable HCV RNA at a prior time point. Specific examples of viral breakthrough responders include patients who have viral breakthroughs between week 4 and week 24. A "relapser responder" is a patient who had undetectable HCV RNA at completion of the peg-IFN with RBV (prior treatment) (generally 6 weeks or less after the last dose of medication), but relapsed during follow-up (e.g., during a 24-week post follow-up). A relapser responder may relapse following 48 weeks of peg-IFN with RBV treatment.

Typical peg-IFN and REV treatment regimens include 12 weeks, 24 weeks, 36 weeks and 48 weeks treatments. Various types of peg-IFN are commercially available, for example, in vials as a prepared, premeasured solution or as a lyophilized (freeze-dried) powder with a separate diluent (mixing fluid). Pegylated interferon alfa-2b (Peg-Intron®) and alfa-2a (Pegasys®) are typical examples. Various types of interferon, including various dosage forms and formulation types, that can be employed in the invention are commercially available (see, e.g., specific examples of interferon described above). For example, various types of interferon are commercially available in vials as a prepared, premeasured solution or as a lyophilized (freeze-dried) powder with a separate diluent (mixing fluid). Pegylated interferon alfa-2b (Peg-Intron®) and alfa-2a (Pegasys®) vary from the other interferons by having molecules of polyethylene glycol (PEG) attached to them. The PEG is believed to cause the interferon to remain in the body longer and thus prolongs the effects of the interferon as well as its effectiveness. Pegylated interferon is generally administered by injection under the skin (subcutaneous). Pegasys® comes as an injectable solution in pre-filled syringes or in vials. The usual dose of Pegasys® is 180 μg, taken once a week. PEG-Intron® generally comes in a pre-filled pen that contains powder and sterile water; pushing down on the pen mixes them together. The dose of PEG-Intron® generally depends on weight-1.5 μg per kilogram (a range of between about 50 and about 150 μg total), taken once a week. In certain embodiments, a pegylated interferon, e.g., pegylated interferon-alpha 2a or pegylated interfero-alpha 2b, is employed in the invention. Typically, interferon can be dosed according to the dosage regimens described in its commercial product labels.

Ribavirin is typically administered orally, and tablet forms of ribavirin are currently commercially available. General standard, daily dose of ribavirin tablets (e.g., about 200 mg tablets) is about 800 mg to about 1200 mg (according to the dosage regimens described in its commercial product labels).

VX-950 may be prepared in general by methods known to those skilled in the art (see, e.g., WO 02/18369). Any suitable formulations known in the art can be used in the invention. For example, formulations described in WO 2005/123075, WO 2007/109604, WO 2007/109605 and WO 2008/080167 can be employed in the invention. A specific formulation that can be used in the invention is exemplified in Example 6. Other specific examples include:

| | |
|---|---|
| VX-950 | 49.5 wt % |
| HPMC 40 cp | 49.5 wt % |
| SLS | 1 wt % |
| VX-950 | 49.5 wt % |
| HPC | 49.5 wt % |
| SLS | 1 wt % |
| VX-950 | 49.5 wt % |
| PVP K30 | 49.5 wt % |
| SLS | 1 wt % |

| VX-950 Solid Dispersion | | |
|---|---|---|
| % (w/w) | Ingredient | |
| 49.5 | VX-950 | Spray- |
| 49.5 | PVP K29/32 | dried from |
| 1 | SLS | a MeCl$_2$ solution | wherein HPMC (Hydroxypropyl Methylcellulose 60SH 50cP (Biddle Sawyer or Shin-Etsu Metolose, HPMC60SHSO) (Hypromellose Acetate Succinate, HG grade, Shin-Etsu Chemical Co.) HPC (hydroxypropyl cellulose), PVP (polyvinylpyrrolidone) and SLS (Sodium Lauryl Sulfate) are as described in WO 2005/123075. In certain embodiments, the solid dispersion shown above can be suspended in a 1% HPMC, 0.002% simethicone solution (1 wt % HPMC, 0.002 wt % simethicone and 99 wt % water). Additional examples include 1:1 VX950: PVPK30, 1 wt % SLS (Refreshed Tox.); Niro-49 wt % HPMCAS/1 wt % SLS/1 wt % SDBS/49% VX-950; 40.5 wt % PVP-VA/10 wt % ETPGS/49.5 wt % VX-950; 40.5 wt % HPMC/10 wt % ETPGS/49.5 wt % VX-950; 49 wt % VX950, 49 wt % HPMCAS, 1 wt % SLS, 1 wt % SDBS; and 49 wt % VX950, 16 wt % HPPh, 33 wt % HPC, 1 wt % SLS, wt % SDBS, wherein PVPK30 (Polyvinyl Pyrrolidone K30), SDBS (sodium dodecyl benzene sulfonate), HPMCAS (Hydroxypropyl Methylcellulose Acetate Succinate), Vitamin ETPGS, PVP (polyvinylpyrrolidone) and SLS (Sodium Lauryl Sulfate), and details of the preparation of these formulations can be found in WO 2005/123075. Additional examples include those described in WO 2007/109604:

a solid dispersion comprising 55 wt % VX-950, 24.4 wt % HPMCAS-HG (Hydroxypropyl Methylcellulose Acetate Succinate, JPE (Biddle Sawyer or Shin-Etsu HPMCAS-HG grade), 19.6 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 55 wt % VX-950, 14.7 wt % HPMCAS-HG (Hydroxypropyl Methylcellulose Acetate Succinate, JPE (Biddle Sawyer or Shin-Etsu HPMCAS-HG grade), 29.3 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 60 wt % VX-950, 24.4 wt % HPMCAS-HG (Hydroxypropyl Methylcellulose Acetate Succinate, JPE (Biddle Sawyer or Shin-Etsu HPMCAS-HG grade), 14.6 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 65 wt % VX-950, 17 wt % HPMCAS-HG (Hydroxypropyl Methylcellulose Acetate Succinate, JPE (Biddle Sawyer or Shin-Etsu HPMCAS-HG grade), 17 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 70 wt % VX-950, 9.7 wt % HPMCAS-HG (Hydroxypropyl Methylcellulose Acetate Succinate, JPE (Biddle Sawyer or Shin-Etsu HPMCAS-HG grade), 19.3 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 60 wt % VX-950, 39 wt % HPMCAS-HG (Hydroxypropyl Methylcellulose Acetate Succinate, JPE (Biddle Sawyer or Shin-Etsu HPMCAS-HG grade), and 1 wt % Sodium Lauryl Sulfate (SLS);

a solid dispersion comprising 49.5 wt % VX-950, 24.5 wt % HPMCAS-HG (Hydroxypropyl Methylcellulose Acetate Succinate, JPE (Biddle Sawyer or Shin-Etsu HPMCAS-HG grade), 24.5 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 83 wt % VX-950, 8 wt % HPMCAS-HG (Hydroxypropyl Methylcellulose Acetate Succinate, JPE (Biddle Sawyer or Shin-Etsu HPMCAS-HG grade), 8 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 49.5 wt % VX-950, 24.5 wt % HPMCAS-HG (Hydroxypropyl Methylcellulose Acetate Succinate, JPE (Biddle Sawyer or Shin-Etsu HPMCAS-HG grade), 24.5 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 70 wt % VX-950, 14.5 wt % HPMCAS-HG (Hydroxypropyl Methylcellulose Acetate Succinate, JPE (Biddle Sawyer or Shin-Etsu HPMCAS-HG grade), 14.5 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 65 wt % VX-950, 14.6 wt % HPMCAS-HG (Hydroxypropyl Methylcellulose Acetate Succinate, JPE (Biddle Sawyer or Shin-Etsu HPMCAS-HG grade), 19.4 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 65 wt % VX-950, 9.7 wt % HPMCAS-HG (Hydroxypropyl Methylcellulose Acetate Succinate, JPE (Biddle Sawyer or Shin-Etsu HPMCAS-HG grade), 24.3 wt % HPMC-60SH (Hydroxypropyl Methylcellulose. 60SH 50cP (Biddle Sawyer or Shin-Etsu Metolose, HPMC60SHSO), and 1 wt % Sodium Lauryl Sulfate (SLS);

a solid dispersion comprising 60 wt % VX-950, 19.5 wt % HPMCAS-HG (Hydroxypropyl Methylcellulose Acetate Succinate, JPE (Biddle Sawyer or Shin-Etsu HPMCAS-HG grade), 19.5 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 60 wt % VX-950, 14.6 wt % HPMCAS-HG (Hydroxypropyl Methylcellulose Acetate Succinate, JPE (Biddle Sawyer or Shin-Etsu HPMCAS-HG grade), 24.4 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 70 wt % VX-950, 9.7 wt % HPMCAS-HG (Hydroxypropyl Methylcellulose Acetate Succinate, JPE (Biddle Sawyer or Shin-Etsu HPMCAS-HG grade), 19.3 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 49.5 wt % VX-950, 24.5 wt % HPMCAS-HG (Hydroxypropyl Methylcellulose Acetate Succinate, JPE (Biddle Sawyer or Shin-Etsu HPMCAS-HG grade), 24.5 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 83 wt % VX-950, 8 wt % HPMCAS-HG (Hydroxypropyl Methylcellulose Acetate Succinate, JPE (Biddle Sawyer or Shin-Etsu HPMCAS-HG grade), 8 wt % HPMC-60SH (Hydroxypropyl Methylcellulose 60SH 50cP (Biddle Sawyer or Shin-Etsu Metolose, HPMC60SH50), and 1 wt % Sodium Lauryl Sulfate (SLS);

a solid dispersion comprising 49.5 wt % VX-950, 49.5 wt % HPMCAS-HG (Hydroxypropyl Methylcellulose Acetate Succinate, JPE (Biddle Sawyer or Shin-Etsu HPMCAS-HG grade), and 1 wt % Sodium Lauryl Sulfate (SLS);

a solid dispersion comprising 83 wt % VX-950, 16 wt % HPMCAS-HG (Hydroxypropyl Methylcellulose Acetate Succinate, JPE (Biddle Sawyer or Shin-Etsu HPMCAS-HG grade), and 1 wt % Sodium Lauryl Sulfate (SLS);

a solid dispersion comprising 82.44 wt % VX-950, 15.89 wt % HPMCAS-HG (Hydroxypropyl Methylcellulose Acetate Succinate, JPE (Biddle Sawyer or Shin-Etsu HPMCAS-HG grade), and 1.67 wt % Sodium Lauryl Sulfate (SLS);

a solid dispersion comprising 49.5 wt % VX-950, 24.75 wt % HPMCAS-HG (Hydroxypropyl Methylcellulose Acetate Succinate, JPE (Biddle Sawyer or Shin-Etsu HPMCAS-HG grade), 24.75 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS).

a solid dispersion comprising 60 wt % VX-950, 24.6 wt % HPMCAS-HG (Hydroxypropyl Methylcellulose Acetate Succinate, JPE (Biddle Sawyer or Shin-Etsu HPMCAS-HG grade), 14.4 wt % HPMC-60SH (Hydroxypropyl Methylcellulose 60SH 50cP (Biddle Sawyer or Shin-Etsu Metolose, HPMC60SHSO), and 1 wt % Sodium Lauryl Sulfate (SLS);

a solid dispersion comprising 60 wt % VX-950, 39 wt % HPMCAS-HG (Hydroxypropyl Methylcellulose Acetate Succinate, JPE (Biddle Sawyer or Shin-Etsu HPMCAS-HG grade), and 1 wt % Sodium Lauryl Sulfate (SLS); and a solid dispersion comprising 49.5 wt % VX-950, 49.5 wt % HPMCAS-HG (Hydroxypropyl Methylcellulose Acetate Succinate, JPE (Biddle Sawyer or Shin-Etsu HPMCAS-HG grade), and 1 wt % Sodium Lauryl Sulfate (SLS).

Details of the preparation of these solid dispersions are described in WO 2007/109604. Additional specific examples include tablet formulations containing a spray dried dispersion of VX-950, which are described in WO 2007/109604:

| Component | mg per Tablet | Percent |
|---|---|---|
| Roller compaction blend | | |
| VX950 Spray Dried Dispersion1 | 505.1 | 74.9 |
| Pharmatose DCL 22 (Lactose, USP/NF, PhEur, JP) | 37.5 | 5.6 |
| Ac-Di-Sol (cross carmellose sodium, NF, PhEur, | 24.0 | 3.6 |
| Extragranular addition | | 0.0 |
| Avicel pH 113 | 33.7 | 5.0 |
| Vitamin E TPGS (NF) | 24.0 | 3.6 |
| Ac-Di-Sol (cross carmellose sodium, NF, PhEur, | 16.0 | 2.4 |
| Cabosil M-5 (colloidal silicon dioxide, NF, PhEur) | 8.0 | 1.2 |
| Sodium Stearyl fumarate (NF, PhEur, JP) | 26.0 | 3.9 |
| Total Formulation weight | 674.3 | 100.0 |

Additional specific examples include tablet formulations described in WO2008/080167:

VX950 SD Tableting Experiment Design (Potency: 250 mg VX950)

| Trial # | Vit E type | Vit E type |
|---|---|---|
| A | VitE-TPGS (24 mg) | Granulated VitE on excipients |
| C | VitE-Acetate (48 mg) | Used as is |
| E | Vit E-TPGS(24 mg) | Vit E Spray Congealed |
| F | Vit E-TPGS (24 mg) | Granulated Vit E onto VX950 |

Trial # A Formulation

| Item | Ingredients | Wt/Tablet (mg) | wt % |
|---|---|---|---|
| | Physical mixture | | |
| 1 | Solid Dispersion (73.55% VX950/26.45% HPMCAS) | 339.9 | 66.32 |
| 2 | PHARMATOSE ® DCL 22 (Lactose) | 37.5 | 7.32 |
| 3 | AC-DI-SOL ® (Cross carmellose sodium) | 24.0 | 4.68 |
| 4 | Sodium Stearyl Fumarate | 1.6 | 0.32 |
| 5 | SLS | 3.4 | 0.66 |
| 6 | AVICEL ® pH 113 (Microcrystalline cellulose) | 33.7 | 6.58 |
| 7 | Vitamin E TPGS (granulated on excipients) | 24.0 | 4.68 |
| 8 | AC-DI-SOL ® (Cross carmellose sodium) | 16.0 | 3.12 |
| 9 | Cabosil M-5 (Colloidal silicon dioxide) | 8.0 | 1.56 |
| 10 | Sodium Stearyl Fumarate | 24.4 | 4.76 |
| | Total | 512.5 | 100 |

Note:
VX 950 SD Lot 02
Potency: 250 mg VX950

Trial # C Formulation

| Item | Ingredients | Wt/Tablet (mg) | wt % |
|---|---|---|---|
| | Physical mixture | | |
| 1 | Solid Dispersion (73.55% VX950/26.45% HPMCAS) | 339.9 | 63.36 |
| 2 | PHARMATOSE ® DCL 22 (Lactose) | 37.5 | 6.99 |
| 3 | AC-DI-SOL ® (Cross carmellose sodium) | 24.0 | 4.47 |
| 4 | Sodium Stearyl Fumarate | 1.6 | 0.30 |
| 5 | SLS | 3.4 | 0.63 |
| 6 | AVICEL ® pH 113 (Microcrystalline cellulose) | 33.7 | 6.28 |
| 7 | Vitamin E-Acetate | 48.0 | 8.95 |
| 8 | AC-DI-SOL ® (Cross carmellose sodium) | 16.0 | 2.98 |
| 9 | Cabosil M-5 (Colloidal silicon dioxide) | 8.0 | 1.49 |
| 10 | Sodium Stearyl Fumarate | 24.4 | 4.54 |
| | Total | 536.5 | 100 |

Trial# E Formulation

| Item | Ingredients | Wt/Tablet (mg) | wt % |
|---|---|---|---|
| | Physical mixture | | |
| 1 | Solid Dispersion (73.55% VX950/26.45% HPMCAS) | 339.9 | 66.32 |
| 2 | PHARMATOSE ® DCL 22 (Lactose) | 37.5 | 7.32 |
| 3 | AC-DI-SOL ® (Cross carmellose sodium) | 24.0 | 4.68 |
| 4 | Sodium Stearyl Fumarate | 1.6 | 0.32 |
| 5 | SLS | 3.4 | 0.66 |
| 6 | AVICEL ® pH 113 (Microcrystalline cellulose) | 33.7 | 6.58 |
| 7 | Vitamin E Spray Congealed | 24.0 | 4.68 |
| 8 | AC-DI-SOL ® (Cross carmellose sodium) | 16.0 | 3.12 |
| 9 | Cabosil M-5 (Colloidal silicon dioxide) | 8.0 | 1.56 |
| 10 | Sodium Stearyl Fumarate | 24.4 | 4.76 |
| | Total | 512.5 | 100 |

Note:
VX 950 SD Lot 02
Potency: 250 mg
VX950

Trial # F Formulation

| Item | Ingredients | Wt/Tablet (mg) | wt % |
|---|---|---|---|
| 1 | Solid Dispersion (73.55% VX950/26.45% HPMCAS) | 339.9 | 66.32 |
| 2 | Vitamin E granulated onto dispersion | 24.0 | 4.68 |
| 3 | PHARMATOSE ® DCL 22 (Lactose) | 37.5 | 7.32 |
| 4 | AC-DI-SOL ® (Cross carmellose sodium) | 24.0 | 4.68 |
| 5 | Sodium Stearyl Fumarate | 1.6 | 0.32 |
| 6 | SLS | 3.4 | 0.66 |
| 7 | AVICEL ® pH 113 (Microcrystalline cellulose) | 33.7 | 6.58 |
| 8 | AC-DI-SOL ® (Cross carmellose sodium) | 16.0 | 3.12 |
| 9 | Cabosil M-5 (Colloidal silicon dioxide) | 8.0 | 1.56 |
| 10 | Sodium Stearyl Fumarate | 24.4 | 4.76 |
| | Total | 512.5 | 100 |

Note:
VX 950 SD Lot 02
Potency: 250 mg
VK950

All cited documents are incorporated herein by reference.

In order that this invention be more fully understood, the following preparative and testing examples are set forth. These examples are for the purpose of illustration only and are not to be construed as limiting the scope of the invention in any way.

Example 1

HCV Replicon Cell Assay Protocol

Cells containing hepatitis C virus (HCV) replicon were maintained in DMEM containing 10% fetal bovine serum (FBS), 0.25 mg per ml of G418, with appropriate supplements (media A).

On day 1, replicon cell monolayer was treated with a trypsin:EDTA mixture, removed, and then media A was diluted into a final concentration of 100,000 cells per ml wit. 10,000 cells in 100 μl were plated into each well of a 96-well tissue culture plate, and cultured overnight in a tissue culture incubator at 37° C.

On day 2, compounds (in 100% DMSO) were serially diluted into DMEM containing 2% FBS, 0.5% DMSO, with appropriate supplements (media B). The final concentration of DMSO was maintained at 0.5% throughout the dilution series.

Media on the replicon cell monolayer was removed, and then media B containing various concentrations of compounds was added. Media B without any compound was added to other wells as no compound controls.

Cells were incubated with compound or 0.5% DMSO in media B for 48 hours in a tissue culture incubator at 37° C. At the end of the 48-hour incubation, the media was removed, and the replicon cell monolayer was washed once with PBS and stored at −80° C. prior to RNA extraction.

Culture plates with treated replicon cell monolayers were thawed, and a fixed amount of another RNA virus, such as Bovine Viral Diarrhea Virus (BVDV) was added to cells in each well. RNA extraction reagents (such as reagents from RNeasy kits) were added to the cells immediately to avoid degradation of RNA. Total RNA was extracted according the instruction of manufacturer with modification to improve extraction efficiency and consistency. Finally, total cellular RNA, including HCV replicon RNA, was eluted and stored at −80° C. until further processing.

A TAQMAN real-time RT-PCR quantification assay was set up with two sets of specific primers and probe. One was for HCV and the other was for BVDV. Total RNA extractants from treated HCV replicon cells was added to the PCR reactions for quantification of both HCV and BVDV RNA in the same PCR well. Experimental failure was flagged and rejected based on the level of BVDV RNA in each well. The level of HCV RNA in each well was calculated according to a standard curve run in the same PCR plate. The percentage of inhibition or decrease of HCV RNA level due to compound treatment was calculated using the DMSO or no compound control as 0% of inhibition. The IC50 (concentration at which 50% inhibition of HCV RNA level is observed) was calculated from the titration curve of any given compound.

VX-950 demonstrated significant activity in the replicon assay. VX-950 was shown to have an $IC_{50}$ of 240 ng/ml and $IC_{90}$ of 476 ng/ml.

Example 2

HCV Ki Assay Protocol

HPLC Microbore Method for Separation of 5AB Substrate and Products
Substrate:

SEQ ID NO: 1
NH$_2$-Glu-Asp-Val-Val-(alpha)Abu-Cys-Ser-Met-Ser-Tyr-COOH.

A stock solution of 20 mM 5AB (or concentration of your choice) was made in DMSO w/0.2M DTT. This was stored in aliquots at −20 C.

Buffer: 50 mM HEPES, pH 7.8; 20% glycerol; 100 mM NaCl
Total assay volume was 100 μL

|  | X1 (μL) | conc. in assay |
|---|---|---|
| Buffer | 86.5 | See above |
| 5 mM KK4A | 0.5 | 25 μM |
| 1M DTT | 0.5 | 5 mM |
| DMSO or inhibitor | 2.5 | 2.5% v/v |
| 50 μM tNS3 | 0.05 | 25 nM |
| 250 μM 5AB (initiate) | 20 | 25 μM |

The buffer, KK4A, DTT, and tNS3 were combined; distributed 78 μL each into wells of 96 well plate. This was incubated at 30° C. for bout 5-10 minutes.

2.5 μL of appropriate concentration of test compound was dissolved in DMSO (DMSO only for control) and added to each well. This was incubated at room temperature for 15 min.

The reaction was initiated by addition of 20 μL of 250 μM 5AB substrate (25 μM concentration is equivalent or slightly lower than the Km for 5AB). After incubating the reaction mixture for 20 min at 30° C., the reaction was terminated by addition of 25 μL of 10% TFA, and the mixture was transferred 120 μL aliquots to HPLC vials for analysis.

SMSY product was separated from substrate and KK4A by the following method:
Microbore Separation Method:
Instrumentation: Agilent 1100
Degasser G1322A
Binary pump G1312A
Autosampler G1313A
Column thermostated chamber G1316A
Diode array detector G1315A Column:
Phenomenex Jupiter; 5 micron C18; 300 angstroms; 150×2 mm; P/o 00E-4053-B0
Column thermostat: 40 C
Injection volume: 100 μL
Solvent A=HPLC grade water+0.1% TFA
Solvent B=HPLC grade acetonitrile+0.1% TFA

| Time (min) | % B | Flow (ml/min) | Max press. |
|---|---|---|---|
| 0 | 5 | 0.2 | 400 |
| 12 | 60 | 0.2 | 400 |
| 13 | 100 | 0.2 | 400 |
| 16 | 100 | 0.2 | 400 |
| 17 | 5 | 0.2 | 400 |

Stop time: 17 min
Post-run time: 10 min.

Example 3

VX-950 was examined in a randomized, double-blind, placebo-controlled single-dose escalation study. 25 healthy male volunteers were enrolled. Each subject received multiple single doses of VX-950 at least 7 days apart, 3 doses of VX-950 at increasing dose levels and 1 dose of placebo.

Doses of 25 mg to 1250 mg were evaluated. A dose escalation scheme was used that combined dose doubling and modified Fibonacci to be aggressive in the lower dose range and conservative in the higher dose range.

VX-950 was well tolerated at all dose levels and no serious adverse events were reported during the study. There did not appear to be an increase in adverse events with increasing dose levels.

A pharmacokinetics analysis was performed using the statistical moment approach. Pharmacokinetic analysis showed that VX-950 was absorbed with a median $t_{max}$ of 3 hours. Less than 2% of VX-950 was eliminated unchanged in the urine, indicating that the drug is primarily eliminated via the metabolic route.

Example 4

Infectious Virus Assay

VX-950 demonstrated an $IC_{50}$ of 196 ng/ml in the infectious virus assay.

Example 5

VX-950 was examined in a randomized, placebo-controlled, multiple-dose, blinded, dose escalation study in 24 healthy subjects and 34 Hepatitis C positive subjects.

Healthy subjects were divided into 3 panels of 8 subjects each. In each panel, 6 subjects received VX-950 and 2 subjects received placebo. Healthy subjects were dosed with VX-950 at 450 mg, 750 mg, or 1250 mg q8h for 5 consecutive days. The healthy subjects were between the ages of 18-65 years (inclusive) and were Hepatitis B, Hepatitis C, and HIV negative. The males had a body mass index of 18.5-29.0 kg/m$^2$ (inclusive). The females had a body mass index of 18.5-32.5 kg/m$^2$ (inclusive).

Hepatitis C (genotype 1) positive subjects were divided into 3 panels of 12 subjects each. In each panel, 10 subjects received VX-950 and 2 subjects received placebo; in the 750 mg q8h group, 2 subjects withdrew prior to dosing so 8 subjects received the VX-950 and 2 received placebo. The HCV positive subjects were dosed with VX-950 at 450 mg or 750 mg, q8h or 1250 mg, q12h for 14 consecutive days.

VX-950 was well tolerated at all dose levels and no serious adverse events were reported during the study; mild and moderate adverse events were reported. All subjects completed the study.

Among the HCV positive subjects, the following percentages of subjects were treatment-naïve in the placebo, 450 mg q8h, 750 mg q8h, and 1250 mg q12h groups: 33.2%, 10%, 12.5%, and 30%, respectively.

The HCV positive subjects were tested post-treatment to monitor HCV RNA levels return to baseline.

TABLE 1

Subject Baseline Characteristics

| | | VX-950 | | |
|---|---|---|---|---|
| | Placebo (n = 6) | 450 mg q8h (n = 10) | 750 mg q8h (n = 8) | 1250 mg q12h (n = 10) |
| Sex, n (%) | | | | |
| Male | 3 (50.0) | 8 (80.0) | 3 (37.5) | 8 (80.0) |
| Female | 3 (50.0) | 2 (20.0) | 5 (62.5) | 2 (20.0) |
| Race, n (%) | | | | |
| Caucasian | 6 (100) | 10 (100) | 8 (100) | 10 (100) |
| Age, years | | | | |
| Median | 54.0 | 47.0 | 52.0 | 43.5 |
| Range | 31-64 | 33-64 | 46-64 | 25-62 |
| BMI, kg/m² | | | | |
| Median | 24.8 | 25.8 | 27.0 | 22.2 |
| Range | 21.0-29.0 | 22.6-28.4 | 21.1-29.4 | 21.2-24.3 |
| HCV RNA, $\log_{10}$ IU/mL | | | | |
| Mean ± SD | 6.28 ± 0.47 | 6.54 ± 0.50 | 6.18 ± 0.47 | 6.46 ± 0.41 |
| Approximate years | | | | |
| HCV infection, mean ± SD | 7.3 ± 7.6 | 9.2 ± 11.5 | 7.2 ± 7.6 | 6.9 ± 6.7 |
| HCV subtype, n (%) | | | | |
| 1* | 1 (16.7) | 0 | 2 (25.0) | 1 (10.0) |
| 1a | 2 (33.3) | 3 (30.0) | 1 (12.5) | 5 (50.0) |
| 1b | 3 (50.0) | 7 (70.0) | 5 (62.5) | 4 (40.0) |
| Prior hepatits C treatment, n (%) | 4 (66.7) | 9 (90.0) | 7 (87.5) | 7 (70.0) |

*Samples from 4 patients were classified as genotype 1 because the assay could not determine whether they were genotype 1a or 1b.
BMI, body mass index;
HCV, hepatitis C virus;
q8h, every 8 hours;
q12h, every 12 hours;
SD, standard deviation.
HCV RNA change from baseline, study VX04-950-101

TABLE 2

Maximum changes in HCV RNA by Category

| | | VX-950 | | |
|---|---|---|---|---|
| Change From Baseline in HCV RNA ($\log_{10}$ IU/mL) | Placebo (n = 6) | 450 mg q8h (n = 10) | 750 mg q8h (n = 8) | 1250 mg q12h (n = 10) |
| >−1 to <0 | 6 (100.0) | 0 | 0 | 0 |
| >−2 to ≤−1 | 0 | 0 | 0 | 0 |
| >−3 to ≤−2 | 0 | 1 (10.0) | 0 | 1 (10.0) |
| >−4 to ≤−3 | 0 | 7 (70.0) | 3 (37.5) | 9 (90.0) |
| >−5 to ≤−4 | 0 | 0 | 3 (37.5) | 0 |
| ≥−5 | 0 | 2 (20.0) | 2 (25.0) | 0 |

Values are n (%).
q8h, every 8 hours;
q12h, every 12 hours.

Example 6

An oral dosage formulation was prepared as follows. VX-950 and povidone K29/32 were dissolved in methylene chloride, then sodium lauryl sulfate was added and dispersed in the solution to form a homogenous suspension. This suspension was spray-dried using an inlet temperature of 90° C. and an outlet temperature of 56° C., and the product was collected from the cyclone. The spray-dried dispersion was fluid-bed dried at 75° C. for 8 hours. The resultant powder was pre-measured into glass vials, and just prior to dosing was suspended in water (30 mL) for administration to the subjects. In connection with dosing, each vial was washed with 3 separate portions of water, with the total volume of water being 90 mL.

| VX-950 Solid Dispersion | | |
|---|---|---|
| % (w/w) | Ingredient | |
| 49.5 | VX-950 | Spray-dried from $CH_2Cl_2$ |
| 49.5 | PVP K29/32 | |
| 1 | SLS | |

Example 7

Detection of HCV RNA was done using the Roche COBAS TAQMAN HCV/HPS assay, available from Roche molecular Diagnostics. Other assays are available.

Example 8

Serum neopterin concentrations were measured by a quantitative competitive ELISA (ELItest® Neopterin, Brahms, Hennigsdorf, Germany) at pretreatment, at day 7 and 14, and at day 7-10 of follow-up. The lower limit of detection (LLD) was 2 nmol/l.

Example 9

Serum ALT was measured using commercially available methods.

Example 10

VX-950 Validation in Human Plasma

VX-950

Stock solution: 0.961 mg/ml of VX-950 in 2-propanol (10.0 ml)

Diluted stock solution 1: 96.1 μg/ml of VX-950 in 2-propanol (5.00 ml)

Diluted stock solution 2: 9.61 μg/ml of VX-950 in 2-propanol (10.0 ml)

Diluted stock solution 3: 0.961 μg/ml of VX-950 in 2-propanol (10.0 ml)

The stock and diluted stock solutions were stored in capped borosilicate tubes (11.5 ml) at −20° C.

Internal Standard (Compound 1)

Stock solution: 1.00 mg/ml of Compound 1 (a close structural analog of VX-950) in 2-propanol (5.00 ml)

Working solution: 300 ng/ml of Compound 1 in acetonitrile (100 ml)

The stock solution was stored in a capped borosilicate tube (11.5 ml); the working solution in a capped borosilicate bottle (100 ml), all at −20° C.

Sample Preparation

Aliquots of 100 μl of plasma, 100 μl of internal standard working solution (or acetonitrile for blank samples) was added to an extraction tube. After vortex mixing for 30 seconds, 500 μl of toluene was added and extraction was performed by vortex mixing for 30 seconds. After centrifugation at 3000 rpm at +4° C. for 5 minutes, the aqueous layer was frozen in a mixture of acetone and dry ice and the organic layer transferred to another extraction tube. 50 μl of 2,2-dimethoxypropane was added and the samples were evaporated to dryness under nitrogen at approximately +30° C. The residue was redissolved in 300 μl of heptane:acetone (90:10, v/v) [or heptane:THF (80:20, v/v)] by vortex mixing for 60 seconds. The sample was transferred to an injection vial and an aliquot of 60 μl was injected into the chromatographic system.

Chromatographic Conditions

Mobile phase: (Isocratic elution) heptane:acetone:methanol (80:19:1, v/v/v)

Make-up Solvent: acetonitrile:acetone:methanol:formic acid (40:60:1:1, v/v/v/v)

Column temperature: −1° C.

Flow rate: 1.00 ml/min (of which: 0.750 ml/min mobile phase and 0.250 ml/min make-up solvent) (completely transferred to detector)

Injection volume: 60 μl

Autosampler temperature: +3° C.

Example 11

Treatment with PEG-Interferon-Alfa-2a (Peg-IFN) and Ribavirin (RBV) Follow-on Therapy After 28-Day Treatment with VX-950, Peg-IFN, and RBV.

VX-950 combinations were administered to patients to show safety of VX-950 when given in combination with Peginterferon alfa-2a (Peg-IFN) and ribavirin (RBV) and to evaluate the antiviral response during 28 days of dosing. After completion of the 28-day study, all subjects received off-study therapy with Peg-IFN/RBV under the clinical care of their physicians. Here we report the outcome of treatment after this post-study therapy.

This study included 12 treatment-naïve patients infected with genotype 1. All subjects received VX-950 (750 mg q8h), Peg-IFN alfa-2a (180 μg weekly), and RBV (1000 or 1200 mg daily). At the completion of the 28 days, patients began off-study follow-on therapy with Peg-IFN alfa-2a/RBV.

Results: VX-950/Peg-IFN/RBV was well tolerated in the 28-day study, with no serious adverse events. The adverse event profile was consistent with the profile commonly seen with Peg-IFN/RBV therapy. All subjects demonstrated a response to the study drug regimen, with 2 subjects reaching undetectable (<10 IU/mL, Roche TAQMAN® Assay) levels of plasma HCV RNA within 8 days of the start of dosing, and all subjects had undetectable HCV RNA at the end of the 28-day study dosing period. At 12 weeks of follow-on therapy after completing the 28-day study dosing, 11 subjects had undetectable HCV RNA. All subjects continued on Peg-IFN/RBV therapy, and were followed for response in accordance with standard practice. Seven patients received a total of 48 weeks of treatment and achieved SVR. One patient received Peg-IFN/RBV for only 18 weeks (total treatment 22 weeks) before discontinuing, but also achieved SVR. Two patients had viral breakthroughs at 12 weeks and 24 weeks of treatment and two patients have been lost to follow up. In total, 8/10 patients for whom results are available, achieved SVR. The side effect profile observed during the post-study dosing was consistent with the expected profile of Peg-IFN/RBV therapy.

A rapid and substantial antiviral effect of telaprevir was observed, with all subjects achieving undetectable plasma HCV RNA within 28 days of dosing. Eleven subjects maintained undetectable HCV RNA through the first 12 weeks of post-study standard therapy. Eight patients achieved SVR after post-study Peg-IFN/RBV, including 1 who completed only 22 weeks of treatment.

The rapid and substantial initial antiviral effect of telaprevir was maintained by the majority of patients during post-study therapy with PegIFN/RBV. The observation that SVR was achieved in eight patients, including 1 who completed only 22 weeks of treatment, indicates that telaprevir-based regimens may allow increased SVR rates as compared to current therapies.

Example 12

Current treatment for patients with genotype 1 chronic hepatitis C(HCV): 48 weeks of therapy with pegylated interferon-alfa-2a/2b (Peg-IFN-2a) and ribavirin (RBV). Sustained virologic response (SVR): 50% of patients with genotype-1 HCV; Poor tolerability; VX-950 is a specifically-targeted antiviral therapy for HCV (STAT-C) that potently and selectively inhibits the HCV NS3·4A protease.

VX-950 had rapid and profound antiviral activity as a single agent and in combination with Peg-IFN-2a and was well tolerated for 14 days. This Study was designed to provide information on the kinetics of HCV following treatment with VX-950 when administered over 14 days in combination with Peg-IFN-2a. To evaluate the durability of the virologic response in 20 genotype 1 infected patients who were initially randomized to three dosing arms (VX-950 alone vs. VX-950/Peg-IFN-2a vs. Peg-IFN-2a) in a 14-day study and who subsequently received Peg-IFN-2a/RBV off-study.

At the completion of the 14-day study dosing, Peg-IFN-2a and RBV was offered to all patients (n=20).

Post-treatment period included 1-week safety and 12-week HCV RNA level follow-up on-study, and 24-week and 48-week HCV RNA level follow-up off-study. Data presented includes viral response follow-up data (i.e., up to 24 weeks after completion of the study dosing); by this time several subjects had stopped off-study Peg-IFN-2a/RBV therapy. During the off-study treatment period, follow-up visits were conducted at the discretion of the investigators.

This study randomized twenty treatment-naïve patients with chronic genotype 1 hepatitis C infection to three dosing arms (Table 3). At the completion of the 14-day study, 19 of 20 patients chose to begin Peg-IFN-2a/RBV, starting within 5 days of completing the 14-day dosing period. Clinic visits were conducted at the discretion of the investigators, after completion of the 1-week and 12-week study-mandated follow-up visits. Nineteen patients have been followed through 24 weeks after the completion of the study dosing. After discussion with the treating physicians, ten (4 in VX-950 and 6 in VX-950/Peg-IFN-2a) patients stopped Peg-IFN-2a/RBV treatment at 24 weeks. The current disposition of the patients is presented in Table 3.

TABLE 3

Disposition of Patients

| | Placebo + Peg-IFN-2α N | VX-950 N | VX-950 + Peg-IFN-2α N | Total N |
|---|---|---|---|---|
| Enrolled | 4 | 8 | 8 | 20 |
| Dosed | 4 | 8 | 8 | 20 |
| Completed 2 Weeks of Treatment | 4 | 8 | 8 | 20 |
| Off-Study Treatment (Peg-IFN-2a/RBV) | | | | |
| Completed 1-Week Safety Follow-up On-Study | 4 | 8* | 8 | 20 |
| Completed 12-Week Antiviral Follow-up On-Study | 4 | 7 | 8 | 19 |
| Completed 24-Week Antiviral Follow-up Off-Study | 4 | 7 | 8 | 19 |
| Peg-IFN-2a/RBV/Discontinuation at 24 weeks due to decision of patient | 0 | 4 | 6 | 10 |

*One patient declined Peg-IFN-2a/RBV

At the last off-study follow-up day (12 weeks after the last on-study follow-up), all patients who continued with Peg-IFN-2a/RBV, initially randomized in the VX-950 alone and VX-950/Peg-IFN-2a groups had undetectable HCV RNA. Data are presented in Table 101.

TABLE 4

Undetectable HCV RNA by groups during the post study-treatment period

| | HCV RNA below Limit of quantitation[a] (30 IU/mL) n Peg-IFN-2a/RBV On-study | | HCV RNA below Limit of detection[a] (10 IU/Ml) n Peg-IFN-2a/RBV On-Study | | HCV RNA below Undetectable[b] n PEG-IFN-2a/RBV Off-Study 24-week F/U (12 weeks after last on-study follow-up) |
|---|---|---|---|---|---|
| | 1-week F/U | 12-week F/U | 1-week F/U | 12-week F/U | |
| VX-950 (N-7) | 3 | 6 | 1 | 5 | 7 |
| VX-950/Peg-IFN-2a (N-8) | 6 | 8 | 3 | 8 | 8 |
| Peg-IFN-2a (N-4) | 0 | 3 | 0 | 1 | 3 |

[a]COBAS TAQMAN HCV RNA assay, Roche Molecular Diagnostics
[b]Taquran HCV RNA assay (15/IU/MI) and (5IU/MI): off-study Of the 10 patients who stopped post-study Peg-IFN-2a/RBV treatment after 24 weeks total treatment (Table 5): 2 of 4 patients who originally received VX-950 alone demonstrated undetectable plasma HCV RNA level at 12 weeks follow-up after stopping Peg-IFN-2a 5 of 6 patients who originally received VX-950/Peg-IFN-2a demonstrated undetectable plasma HCV RNA level at 12 weeks follow-up after stopping Peg-IFN-2a

TABLE 5

Undetectable HCV RNA by groups following Peg-IFN-2a/RBV discontinuation

| | Undetectable HCV RNA At 24-week off-study Peg-IFN-2a/RBV treatment N | Patients who stopped peg-IFN-2a/RBV at Week 24 n/N | Undetectable HCV RNA at 12-weeks follow-up after stopping Peg-IFN-2a/RBV n/N |
|---|---|---|---|
| VX-950 (N-8) | 7* | 4/7 | 2/4 |
| VX-950/Peg-IFN-2a (N-8) | 8 | 6/8 | 5/6 |
| Peg-IFN-2a (N-4) | 3 | 0/4 | N/A |

*One patient declined Peg-IFN-2a/RBV

At 24-week off-study follow-up all the patients initially randomized in VX-950 groups and continued with Peg-IFN-2a/RBV, maintained undetectable HCV RNA. The 12-week post-treatment (Peg-IFN-2a/RBV) follow-up viral load data are consistent with models which suggest required duration to achieve SVR is related to kinetics of early viral clearance.

SVR was achieved in 10 of 15 patients who received 14 days of therapy of VX-950 optionally in combination with Peg-IFN followed by Peg-IFN with RBV for an additional 22 or 46 weeks.

At week 12, all 8 patients who received an initial combination of VX-950 with PEG-IFN and 5 of 7 patients who received VX-950 alone had undetectable HCV RNA. At week 24, all 15 patients who received VX-950 had undetectable HCV RNA. 10 patients (6 of 8 VX-950 with PEG-IFN and 4 of 7 VX-950 alone) decided to stop PEG-IFN/RBV at week 24 and 5 patients continued treatment of PEG-IFN/RBV for a total of 48 weeks. All groups were followed for an additional 24 weeks. In patients who received at least 14 days of VX-950 (alone or in combination with PEG-IFN) before starting the PEG-IFN with RBV, 7 of 10 patients treated for 24 weeks and 3 of 5 patients treated for 48 weeks achieved SVR.

Example 13

A Study of Telaprevir Combined with Peginterferon-Alfa-2a and Ribavirin in Subjects with Well-Documented Non-Response or Relapse after Previous Peginterferon-Alfa-2a and Ribavirin Treatment: Interim Analysis Patients who have not achieved SVR with prior treatment represent a large unmet medical need in hepatitis C virus management. This is an open-label study of telaprevir, a potent and selective inhibitor of HCV NS3.4A protease, combined with peginterferon-alfa-2a and ribavirin in genotype 1

HCV patients who did not achieve SVR in PR control arms of the Phase 2 PROVE studies. The study aims to determine the antiviral responsiveness to T/PR in well-characterized null and partial responders and relapsers to PR, and assess the correlation between the response to T/PR treatment with the original response to PR.

Null responders (<1 $\log_{10}$ decrease in HCV RNA at wk 4 or <2 $\log_{10}$ decrease at wk 12), partial responders (≥2 $\log_{10}$ decrease at wk 12, detectable HCV RNA at wk 24), and relapsers from the PR arms of the PROVE studies were eligible. Study dosing consists of 12 weeks TVR plus PEG-IFN/RBV, followed by 12 weeks of PEG-IFN/RBV (relapsers or partial responders) (T12/PR24 regimen) or 36 wks (null responders) based on prior response to PR and on-treatment response at the following doses: TVR 750 mg every 8 hours, PEG-IFN 180 μg subcutaneously weekly, RBV 1000 mg or 1200 mg daily. Treatment was discontinued if HCV RNA was >100 IU/mL at wk 4 or >25 IU/mL at wk 12.

Preliminary analysis includes all enrolled patients who received at least one dose of study regimen and who complete at least the Week 4 assessment. HCV RNA levels are measured using the TAQMAN® HCV RNA assay Version 2.0 (Roche Molecular Systems Inc, Branchburg, N.J., USA). The lower limit of quantification (LLOQ) is <25 IU/mL. The lower limit of detection (LOD) is <10 IU/mL (below limit of quantification and without detectable signal for HCV-RNA). Safety assessments are recorded throughout the study and descriptive statistics are used for the preliminary analysis.

72 patients received ≥1 dose of study drugs; 60, 36, and 16 patients completed treatment through wks 4, 8 and 12, respectively. Baseline characteristics (n=59) were: 46 male; median age 52 yrs; 52 Caucasians, 6 Blacks and 1 Hispanic; median baseline HCV RNA 6.8 $\log_{10}$ IU/mL. Virologic responses are shown below:

TABLE 6

Patient Disposition

| Current patient disposition, n | T12/PR24 | T12/PR48 | Not Assigned* |
|---|---|---|---|
| Received ≥1 dose of study drug | 55 | 38 | 21 |
| Patients currently on treatment | 20 | 27 | 7 |
| Completed treatment through Week 4 | 55 | 36 | 13 |
| Completed treatment through Week 8 | 48 | 33 | 5 |
| Completed treatment through Week 12 | 46 | 32 | 1 |
| Completed treatment through Week 16 | 35 | 27 | 1 |
| Completed treatment through Week 20 | 30 | 24 | 0 |
| Completed treatment through Week 24 | 25 | 21 | 0 |

Premature discontinuations during the first 12 weeks are for the following reasons: 6 patients due to Week 4 stopping rule, 2 patients had viral breakthrough (>1 $\log_{10}$ increase or >100 IU/mL HCV RNA) at wk 2; both were wk 4 null responders to prior PR, and 2 patients due to adverse events (1 patient discontinued due to stopping rule). Reported adverse events were as expected for PR, and consistent with T/PR-based regimens in the PROVE studies.

TABLE 7

Baseline characteristics of the patients who reached at least Week 4 assessment.

| | T12/PR24 (n = 55) | T12/PR48 (n = 37) | Not Assigned (n = 15) |
|---|---|---|---|
| Gender, n (%) | | | |
| Male | 37 (67) | 30 (81) | 10 (68) |
| Race, n (%) | | | |
| Caucasian | 50 (91) | 32 (86) | 14 (93) |
| Black | 2 (4) | 5 (13.5) | 1 (7) |
| Other | 3 (5) | — | — |
| Median age, years (range) | 52 [19-60] | 52 [34-63] | 50 [43-62] |
| Median weight, kg (range) | 81 [50-146] | 90 [64-138] | 79 [53-120] |
| Median BMI, kg/m2 (range) | 26 [19-57] | 28 [21-44] | 26 [17-37] |
| HCV RNA Median, log10 IU/mL, (range) | 6.6 [5-7.5] | 6.9 [6-7.7] | 6.5 [5-7.7] |
| HCV RNA >800,000 IU/mL, n (%) | 42 (76) | 37 (100) | 11 (73) |
| Genotype 1a, n (%) | 32 (58) | 24 (65) | 8 (53) |
| Genotype 1b, n (%) | 16 (29) | 12 (32) | 5 (33) |
| Genotype 1 (subtype unknown) | 7 (13) | 1 (3) | 2 (13) |

Two patients (2/60, 3%) developed viral breakthrough. In each case, viral breakthrough occurs at Week 2. Both patients were previously Week-4 Null Responder to P/R. Results of population sequencing for these patients revealed V36M/R155K variants at the time of breakthrough.

No viral breakthrough was observed in the patients who did not meet the Week 4 stopping rule and continued on treatment.

In this analysis of TVR-based therapy in HCV genotype 1 patients with well-characterized null response, partial response or relapse to prior pegylated interferon and ribavirin therapy, at Week 4, 88% achieved HCV RNA <25 IU/mL. All of the patients who continued beyond Week 4 maintained their viral responses through Week 24. Viral breakthrough was infrequent (3%), but more frequent in prior null responders and was identified very early in treatment. The findings show that prior pegylated interferon non-responders, including true null responders, can achieve and maintain profound on-treatment response with the addition of TVR.

TABLE 8

Week 4 HCV RNA by Prior PR Virological Response. Patients are unique in each of the non-response categories.

| | N = 104* | <25 IU/mL, did not meet stopping rule | 25-100 IU/mL did not meet stopping rule | >100 IU/mL met stopping rule |
|---|---|---|---|---|
| Null responder (<1 – log10 drop at Week 4 or <2 – log10 drop in HCV RNA by Week 12) | 48 | 36 (75) | 3 (6) | 9 (19) |
| Partial responder (≥2 – log10 drop at Week 12; detectable RNA at Week 24) | 33 | 32 (97) | 1 (3) | 0 |
| Relapser | 22 | 22 (100) | 0 | 0 |
| Viral Breakthrough | 1 | 1 (100) | 0 | 0 |
| Total | 104 | 91 (88) | 4 (4) | 9 (9) |

TABLE 9

Week 12 HCV RNA by Prior PR Virological Response. Patients are unique in each of the non-response categories.

| | | HCV RNA ≥25 IU/mL, met stopping rule, n (%) | | |
|---|---|---|---|---|
| | N = 104* | <10 IU/mL, did not meet stopping rule | <25 IU/mL detectable | >25 IU/mL |
| Null responder (<1 – log10 drop at Week 4 or <2 – log10 drop in HCV RNA by Week 12) | 48 | 28 (58) | 3 (6) | 4 (8) |
| Partial responder (≥2 – log10 drop at Week 12; detectable RNA at Week 24) | 33 | 26 (79) | 0 | 1 (3) |
| Relapser | 22 | 16 (73) | 0 | 0 |
| Viral Breakthrough | 1 | 1 (100) | 0 | 0 |
| Total | 104 | 71 (68) | 3 (3) | 5 (5) |

These preliminary findings suggest that patients with genotype 1 HCV infection who fail to respond to Peg-IFN-alfa-2a and RBV (including well-documented null responders) can achieve and maintain on-treatment response with a T/PR-based regimen. Follow-up treatment of these patients is ongoing to evaluate the clinical significance of these interim findings in this difficult-to-treat population.

An alternative study can be conducted with relapsers and partial responders to prior PR, who in this current analysis have a Week 4 response that is similar to that observed in treatment-naïve patients. These relapsers and partial responders received the response-driven regimen (12 weeks of VX-950, in combination with 24 or 48 weeks of PR depending on the early viral response). Null responders received 48 weeks of PR.

Example 14

In a randomized, double-blind, placebo-controlled Phase 2b study patients who failed prior treatment with peg-IFN and RBV patients include prior non-responders (including null responders), prior relapsers and prior breakthroughs to peg-IFN and RBV treatment. Patients are randomized to receive a 24-week TVR-based regimen (12 weeks of TVR in combination with peg-IFN and RBV, followed by 12 weeks of peg-IFN and RBV alone). The analysis includes 453 patients that received at least one dose of study drug. In the analysis, 52% (60 of 115) of patients achieve undetectable HCV RNA (<10 IU/mL; Roche TAQMAN) 12 weeks post-treatment (SVR12). Of the 115 patients, 66 are categorized as non-responders to prior treatment (defined as patients who never achieved undetectable HCV RNA during prior treatment, including null responders), 40 are prior relapsers (defined as patients who had undetectable HCV RNA at the completion of prior treatment, but relapsed during follow-up), and 9 are prior breakthroughs (defined as patients who had viral rebound during prior treatment). Among patients receiving the 24-week TVR-based regimen, 41% (27 of 66) of the prior non-responders, 73% (29 of 40) of prior relapsers, and 44% (4 of 9) of prior breakthroughs achieve SVR 12.

TABLE 10

Summary of available on-treatment and post-treatment antiviral data from the 24-week TVR-based regimen. Undetectable HCV-RNA by Response to Prior Peg-IFN/RBV Treatment (PROVE 3 24-week regimen; 12 weeks TVR + peg-IFN + RBV, followed by 12 weeks peg-IFN + RBV); intent-to-treat analysis

| | Week 12 | Week 24 (end of treatment) | SVR 12 (week 36; 12 weeks post-treatment) |
|---|---|---|---|
| Non-responders (n = 66) | 71% | 65% | 41% |
| Relapsers (n = 40) | 88% | 83% | 73% |
| Breakthroughs (n = 9) | 44% | 44% | 44% |
| Total (n = 115) | 75% | 70% | 52% |

In the control arm (n=114), which evaluates 48 weeks of peg-IFN and RBV only, available data indicate that 8% of patients have undetectable HCV RNA at week 12, and 30% have undetectable HCV RNA at week 36 on-treatment (intent-to-treat analysis). In prior studies of peg-IFN and RBV in treatment-failure patients, the proportion of patients who had undetectable HCV RNA at week 36 of treatment has been significantly higher than the proportion who ultimately achieved SVR.

In addition to the 24-week TVR-based regimen that includes ribavirin and the 48 week control arm described above, two other treatment regimens are evaluated in the study: a 24-week TVR treatment arm without ribavirin, and a 48-week treatment aim that includes 24 weeks of TVR dosing in combination with peg-IFN and RBV. The analysis supports the inclusion of ribavirin in future studies of TVR-based regimens in treatment-failure patients, similar to what has been observed in treatment-naïve subjects.

In the analysis, adverse events are similar to those commonly observed with peg-IFN and RBV including fatigue, nausea, rash, headache, gastrointestinal disorders and anemia, and are also consistent with those previously reported in patients being treated with TVR-based therapy in the PROVE 1 and 2 studies in treatment-naïve subjects. Thirteen patients (11%) receiving the 24-week TVR-based treatment regimen discontinue treatment due to adverse events. The most common reason for discontinuation among patients receiving this 24-week TVR-based treatment regimen is rash (7% of patients). In the control arm, 5 patients (4%) discontinue treatment prior to week 36 due to adverse events.

Example 15

In another embodiment, dosing regimens for treating HCV can include 12 weeks of TVR in combination with peg-IFN and RBV, followed by 36 weeks of peg-IFN and REV alone. A randomized, double-blind and placebo-controlled study could include regimens of 48 weeks total treatment duration, in which TVR is administered for 12 weeks, with a goal of maximizing SVR rates.

Example 16

A Phase 2 Study of Telaprevir with Peginterferon-Alfa-2a and Ribavirin in Hepatitis C Genotype 1 Null and Partial Responders and Relapsers Following a Prior Course of Peginterferon-Alfa-2a/b and Ribavirin Therapy: Prove3 Interim Results PROVE3 is a randomized, placebo-controlled Phase 2 study of telaprevir combined with peginterferon-alfa-2a and ribavirin in null and partial responders and relapsers with HCV genotype 1 infection who had previously received and failed PR therapy. Below are results of a planned interim ITT analysis performed when all enrolled patients had completed 36 wks of the study.

Patients were randomized to receive either: T 750 mg q8h, P 180 μg/wk, and R 1000-1200 mg/day for 12 wks followed by PR for 12 wks (T12/PR24); or all 3 drugs for 24 wks followed by PR for 24 wks (T24/PR48); or T and P for 24 wks (T24/P24). The control group was randomized to receive 48 wks of PR, with T-matched placebo for the first 24 wks.

465 patients were enrolled, 453 dosed, 240 completed week 24 and 93 patients completed week 36. 213 patients discontinued prior to week 24: 157 due to the stopping rule (not achieving rapid virologic response (RVR) or early virologic response (EVR); or viral breakthrough occurring) with 69 in PR, 25 in T24/PR48, 44 in T24/P24 and 19 in T12/PR24 arms and 56 due to other reasons (adverse effects, withdrew consent). At Week 36, 5 (4%) patients in PR, 13 (11%) in T12/PR24, 30 (26%) in T24/PR48 and 10 (9%) in T24/P24 discontinued due to adverse effects with skin and gastrointestinal disorders being more frequent in the T-based arms. Preliminary data on the number of patients with undetectable HCV RNA (<10 IU/mL) by prior virologic response to PR regimen are shown below.

TABLE 11

Patients with undetectable HCV RNA (<10 IU/mL) by prior virologic response to PR regimen.

| Prior response Visit, n (%) | PR48 N = 114* | T12/PR24 N = 115 | T24/PR48 N = 113 | T24/P24 N = 111 |
|---|---|---|---|---|
| Non-response (Null or Partial) | | | | |
| Wk 4 | 0/68 | 33/66 (50) | 22/64 (34) | 20/62 (32) |
| Wk 12 | 2/68 (2.9) | 47/66 (71) | 35/64 (55) | 23/62 (37) |
| EoT | N/A | 43/66 (65) | N/A | 21/62 (34) |
| SVR12 | N/A | 27/66 (41) | N/A | 7/62 (11) |
| Relapse | | | | |
| Wk 4 | 0/42 | 32/40 (80) | 29/41 (71) | 28/39 (72) |
| Wk 12 | 7/42 (17) | 35/40 (88) | 32/41 (78) | 32/41 (78) |
| EoT | N/A | 33/40 (83) | N/A | 27/39 (69) |
| SVR12 | N/A | 29/40 (72) | N/A | 14/39 (36) |
| Breakthrough | | | | |
| Wk 4 | 0/3 | 4/9 (44) | 6/8 (75) | 3/10 (30) |
| Wk 12 | 0/3 | 4/9 (44) | 6/8 (75) | 5/50 (50) |
| EoT | N/A | 4/9 (44) | N/A | 3/10 (30) |
| SVR12 | N/A | 4/9 (44) | N/A | 2/10 (20) |

*Data for 1 control group pt missing

T/PR therapy resulted in substantially higher viral response rates (RVR, EVR and SVR12) in prior null and partial responders and relapsers in this study, compared with historical viral response rates with PR. SVR12 rates in prior relapsers were similar to those achieved by treatment-naïve patients treated with T/PR in the PROVE1 and PROVE2 Phase 2 studies. Results suggest that R is an integral part of this retreatment regimen to enhance on-treatment response rates. T12/PR24 safety profile was similar to that seen in treatment-naïve patients.

TABLE 12

Undetectable HCV RNA at Weeks 4, 8, 12, 16, 20 and 24 by Prior PR Virologic Response.

| Prior PR virologic responses in Phase 2 studies* | N = 104 | <10 IU/mL, n/N (%) | | | | | |
|---|---|---|---|---|---|---|---|
| | | Week 4 | Week 8 | Week 12 | Week 16 | Week 20 | Week 24 |
| Null responder (<1-$log_{10}$ drop at Week 4 or <2-$log_{10}$ drop in HCV RNA by Week 12) | 48 | 19 (40) | 29 (60) | 28 (58) | 24 (50) | 23 (48) | 18 (37) |
| Partial responder (≥2-$log_{10}$ drop at Week 12; detectable RNA at Week 24) | 33 | 28 (85) | 26 (79) | 26 (79) | 22 (67) | 18 (54) | 18 (54) |
| Relapser | 22 | 20 (91) | 18 (82) | 16 (73) | 12 (54) | 8 (36) | 5 (23) |
| Viral Breakthrough | 1 | 1 (100) | 0** | 1 (100) | 1 (100) | 0 | 0 |

TABLE 13

Undetectable HCV RNA at Weeks 4, 8, 12, 16, 20 and 24 by Prior PR Virologic Response

| Prior PR virologic responses in Phase 2 studies* | N = 104 | <10 IU/mL, n/N (%) | | | | | |
|---|---|---|---|---|---|---|---|
| | | Week 4 n/N*** | Week 8 n/N | Week 12 n/N | Week 16 n/N | Week 20 n/N | Week 24 n/N |
| Null responder (<1-$log_{10}$ drop at Week 4 or <2-$log_{10}$ | 48 | 19/48 (40) | 29/38 (76) | 28/35 (80) | 24/27 (89) | 23/25 (92) | 18/22 (82) |

TABLE 13-continued

Undetectable HCV RNA at Weeks 4, 8, 12, 16, 20 and 24 by Prior PR Virologic Response

| Prior PR virologic responses in Phase 2 studies* | N = 104 | <10 IU/mL, n/N (%) | | | | | |
|---|---|---|---|---|---|---|---|
| | | Week 4 n/N*** | Week 8 n/N | Week 12 n/N | Week 16 n/N | Week 20 n/N | Week 24 n/N |
| drop in HCV RNA by Week 12) Partial responder (≥2-login drop at Week 12; detectable RNA at Week 24) | 33 | 28/33 (85) | 26/29 (90) | 26/27 (96) | 22/23 (96) | 18/20 (90) | 18/19 (95) |
| Relapser | 22 | 20/22 (91) | 18/18 (100) | 16/16 (100) | 12/12 (100) | 8/8 (100) | 5/5 (100) |
| Viral Breakthrough | 1 | 1 (100) | 0** | 1 (100) | 1 (100) | 0 | 0 |

TABLE 14

Cumulative Virologic Breakthrough* Following T/PR Treatment

| Prior virologic response in PR study | N = 107 | Wk 1 N (%) | Wk 2 N (%) | Wk 3 N (%) | Wk 4 N (%) | Wk 8 N (%) | Wk 12 N (%) | Wk 16 N (%) | Wk 20 N (%) | Wk 24 N (%) |
|---|---|---|---|---|---|---|---|---|---|---|
| Null Response | 49 | 0 (%) | 3 (6%) | 3 (6%) | 5 (10%) | 6 (12) | 7 (14) | 8 (16) | 9 (18) | 10 (20) |
| Partial Response | 33 | 0 (%) | 0 (%) | 0 (%) | 0 (%) | 1 (3) | 1 (3) | 2 (6) | 2 (6) | 2 (6) |
| Relapse | 24 | 0 (%) | 0 (%) | 0 (%) | 0 (%) | 0 (%) | 0 (%) | 0 (%) | 0 (%) | 0 (%) |
| Viral Breakthrough | 1 | 0 (%) | 0 (%) | 0 (%) | 0 (%) | 0 (%) | 0 (%) | 0 (%) | 0 (%) | 0 (%) |

Example 17

Telaprevir in Hepatitis C Genotype-1-Infected Patients with Prior Non-Response, Viral Breakthrough or Relapse to Peginterferon-Alfa-2a/b and Ribavirin Therapy: SVR Results of the PROVE3 Study PROVE3 is a randomized, placebo-controlled Phase 2 study assessing safety and efficacy of telaprevir (T) plus Peginterferon-alfa-2a (P)±Ribavirin (R) in HCV genotype 1 patients who previously failed PR treatment.

Randomization was 1:1:1:1 to: T/PR for 12-wks, then PR for 12-wks (T12/PR24); T/PR for 24-wks, then PR for 24-wks (T24/PR48); T/P for 24-wks (T24/P24); or placebo/PR (P 180 μg/wk, R 1000-1200 mg/day) for 24-wks, then PR for 24-wks (PR48).

Of 453 patients included in ITT analysis, 418 (92%) had baseline HCV RNA ≥800,000 IU/mL, 196 (43%) had cirrhosis or bridging fibrosis and 40 (9%) were black; 235 (52%) patients completed assigned treatment.

The most frequent adverse events that occurred with a greater incidence in T12/PR24 or T24/PR48 than PR48 were fatigue, nausea, headache, rash, pruritus, diarrhea, anemia, insomnia, pyrexia, alopecia, and chills. Grade 3 rash was observed in 7 (6%), 5 (4%), 6 (5%) and 1 (1%) patients in T12/PR24, T24/PR48, T24/P24, and PR48, respectively. Grade 3 anemia was observed in 0 (0%), 7 (6%), 1 (1%) and 1 (1%) patients in T12/PR24, T24/PR48, T24/P24 and PR48, respectively. Eleven (10%), 29 (25%), 10 (9%), and 5 (4%) patients discontinued due to AEs in T12/PR24, T24/PR48, T24/P24, and PR48, respectively.

SVR rates in all treatment groups receiving T/PR regimens were significantly higher than with PR48. The general safety profile of T12/PR24 was similar to that observed in treatment-naïve patients. The higher relapse rate in T12/PR24 compared with T24/PR48 may warrant a total of 48-wks of PR in treatment-experienced patients.

TABLE 15

Patients achieving SVR (undetectable HCV RNA 24 weeks after treatment), N (%)

| | T12/PR24 n/N (%) | T24/PR48 n/N (%) | T24/P24 n/N (%) | PR48 n/N (%) |
|---|---|---|---|---|
| All Patients (*statistical comparison to PR48) | 59/115 (51) (p < 0.001) | 59/113 52 (p < 0.001) | 26/111 23 (p = 0.035) | 16/114 14 |
| Prior Relapsers | 29/42 (69) | 31/41 (76) | 16/38 (42) | 8/41 (20) |
| Prior Non-responders (never undetectable) | 26/66 (39) | 24/64 (38) | 6/62 (10) | 6/68 (9) |
| Prior Breakthroughs | 4/7 (57) | 4/8 (50) | 4/11 (36) | 2/5 (40) |

TABLE 16

| Reasons for treatment failure in this study, N (%) | | | | |
|---|---|---|---|---|
| | T12/PR24 n/N (%) | T24/PR48 n/N (%) | T24/P24 n/N (%) | PR48 n/N (%) |
| Relapse | 26/87 (30) | 10/76 (13) | 32/60 (53) | 18/34 (53) |
| Viral breakthrough | 12/115 (10) | 8/113 (7) | 13/111 (12) | 1/114 (1) |
| Protocol-defined stopping rules | 17/115 (15) | 26/113 (23) | 41/111 (37) | 67/114 (59) |

Figure 13:
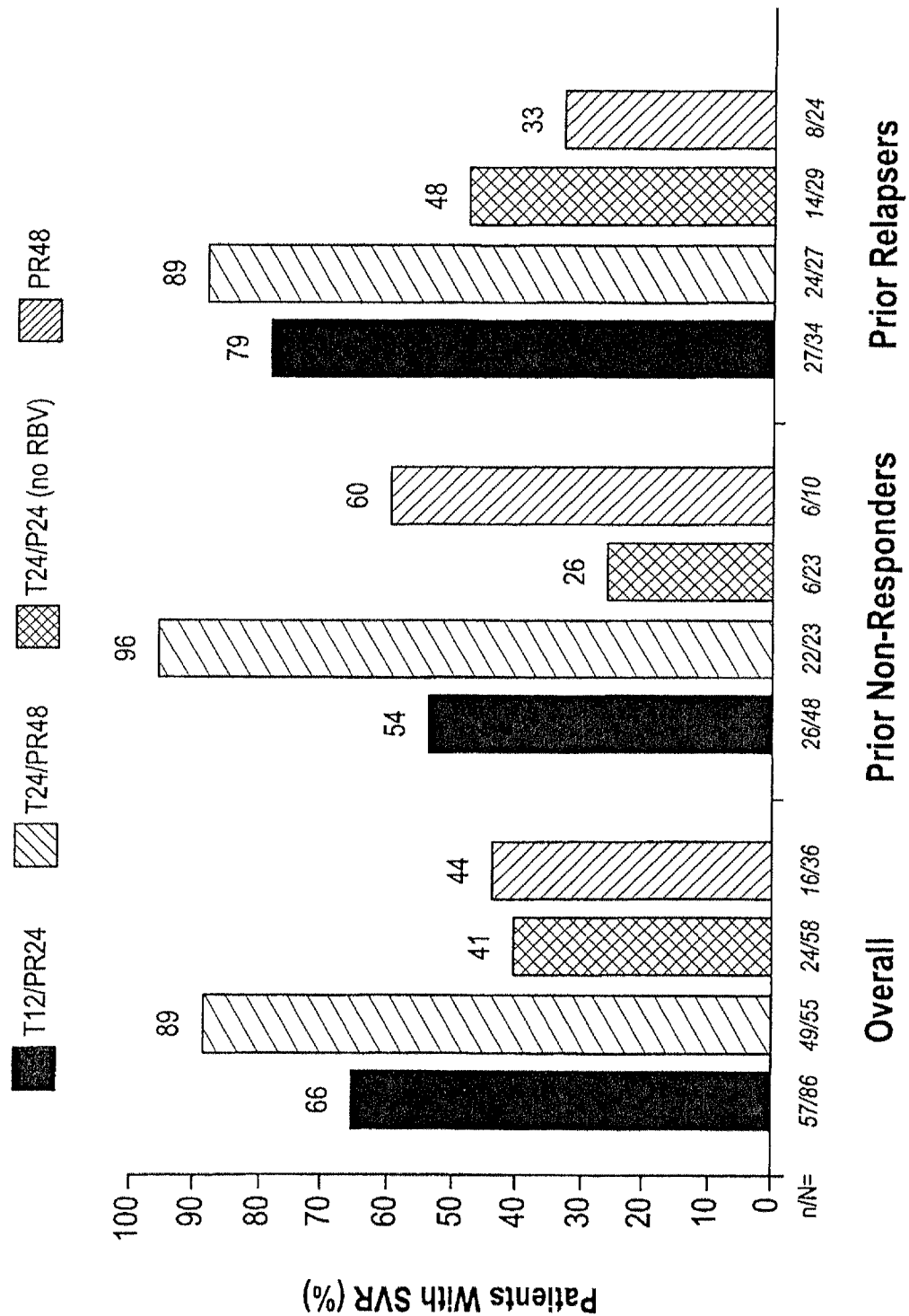
FIG. 13 depicts SVR rates in patients who completed assigned treatment.
Figure 14:
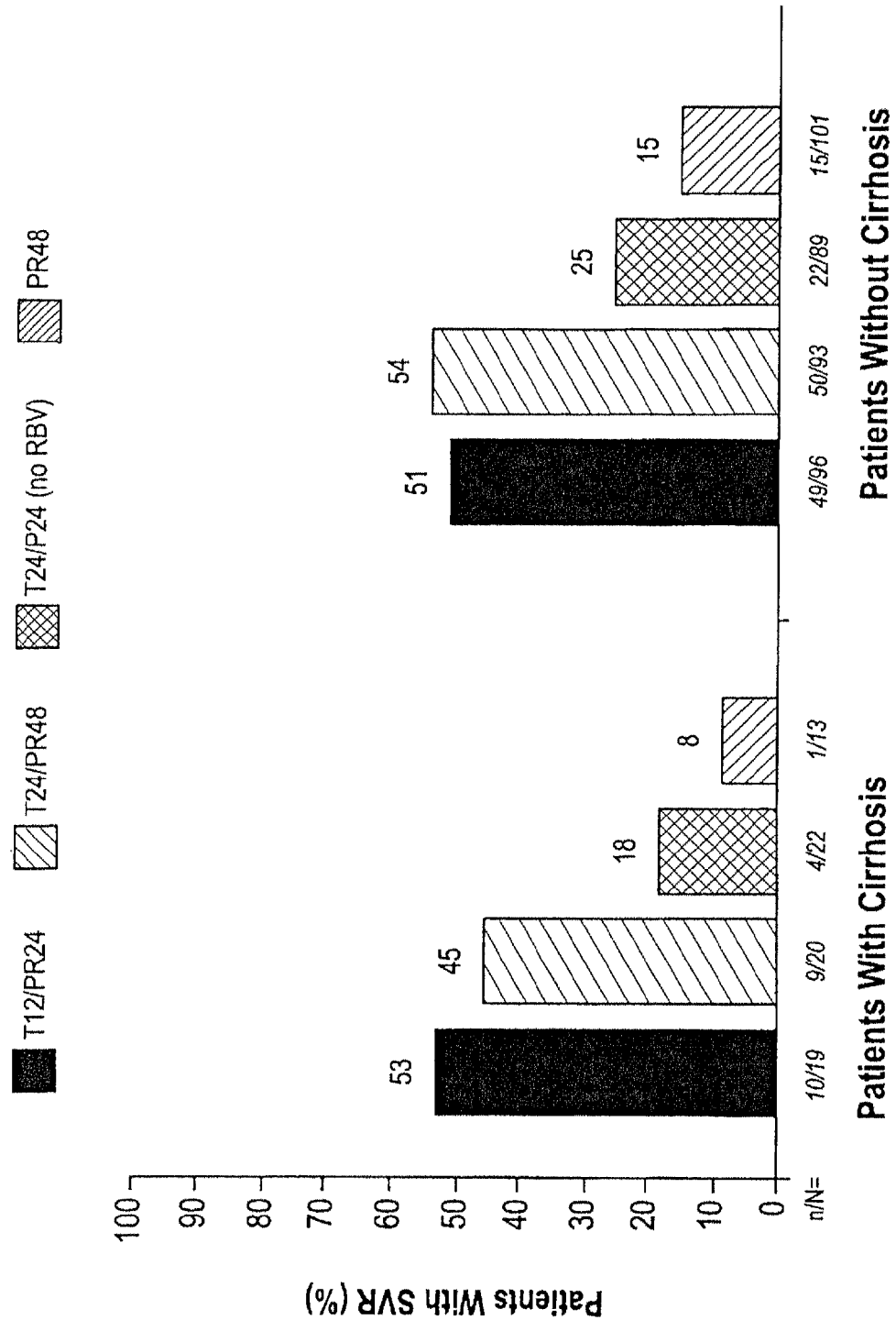
FIG. 14 depicts SVR rates by cirrhosis status (ITT analysis).
Figure 15:
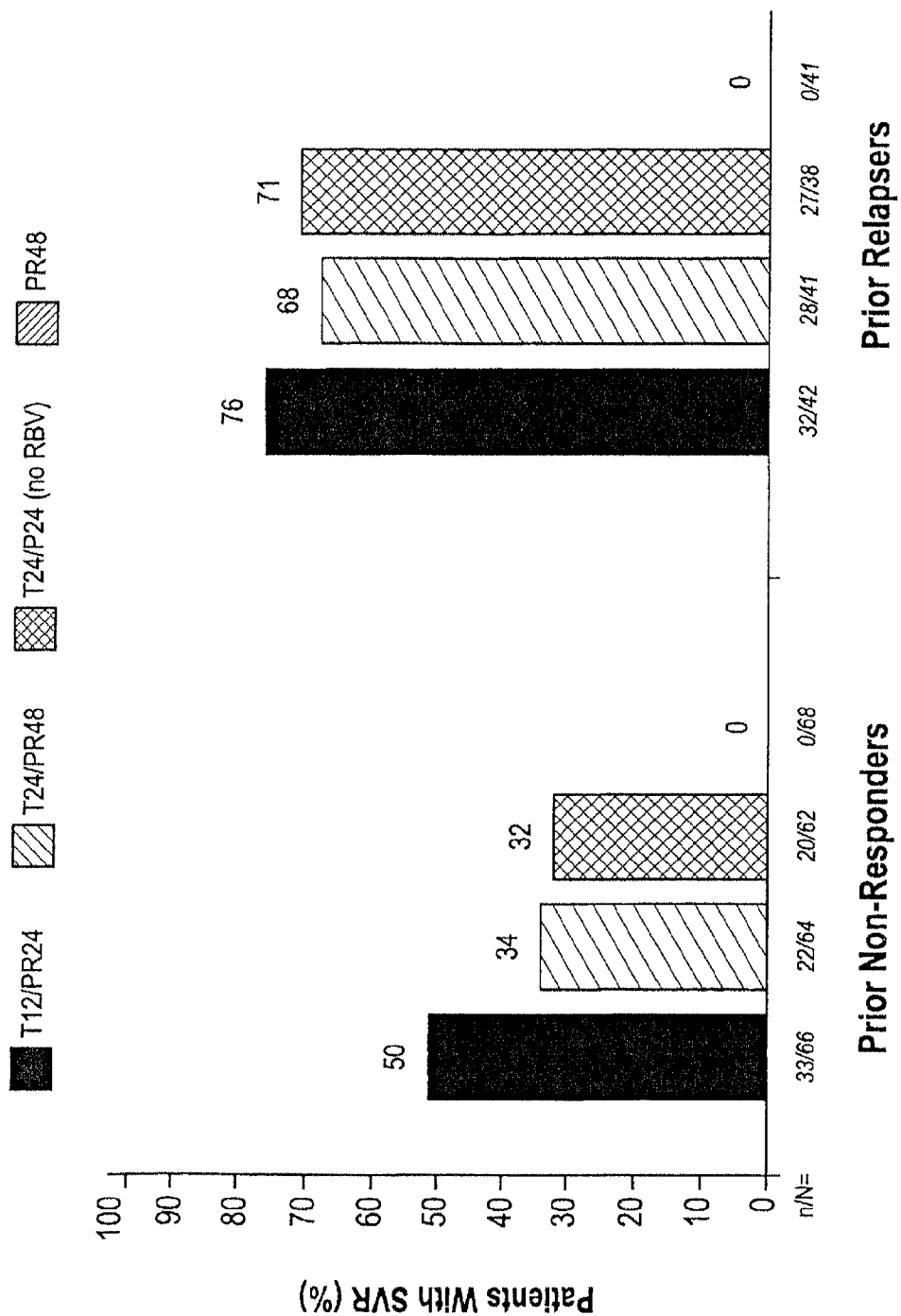
FIG. 15 depicts undetectable HCV RNA at RVR (Week 4) by treatment group and prior response (ITT).
Figure 16:
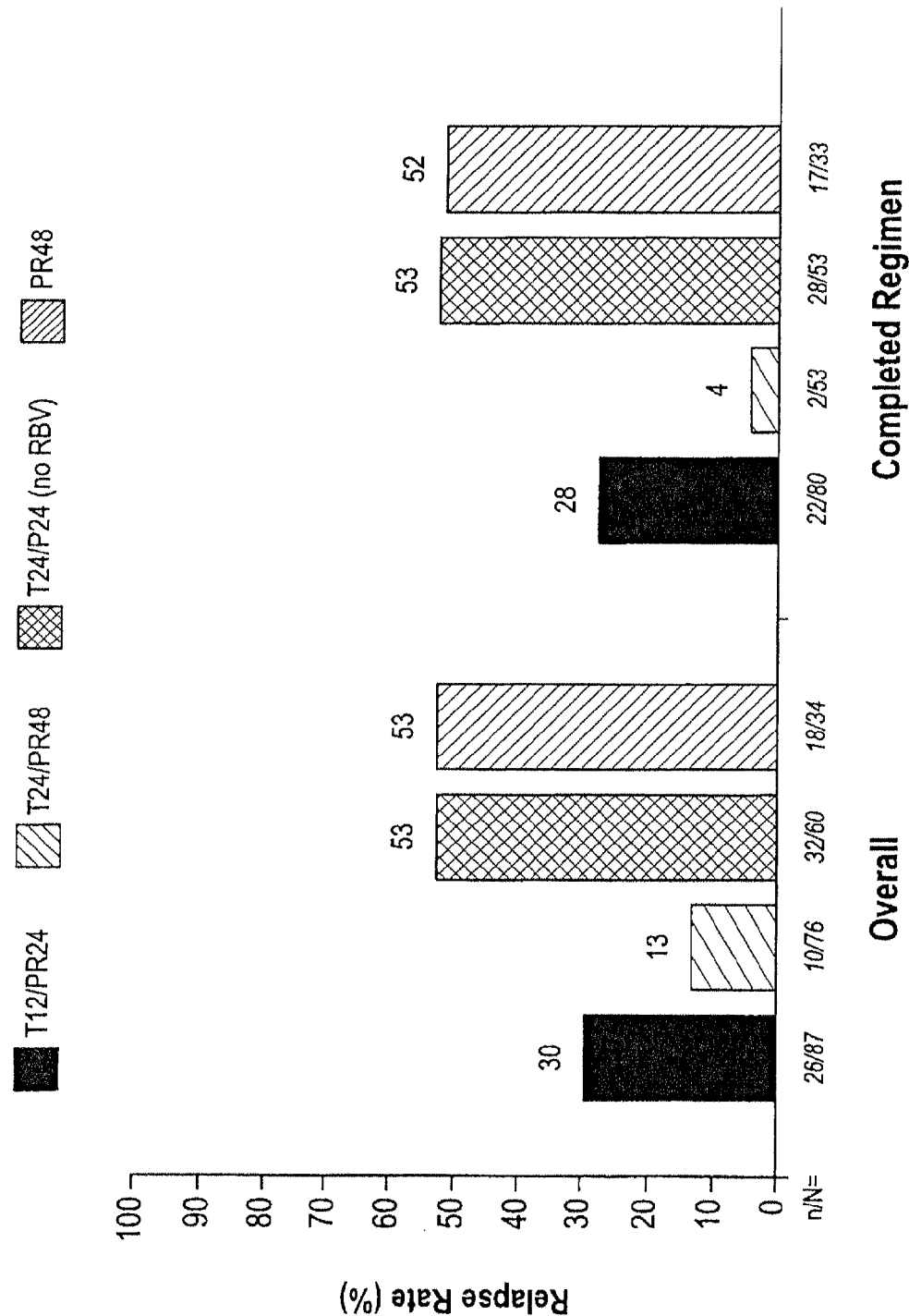
FIG. 16 depicts relapse rates by treatment group.
Figure 17:
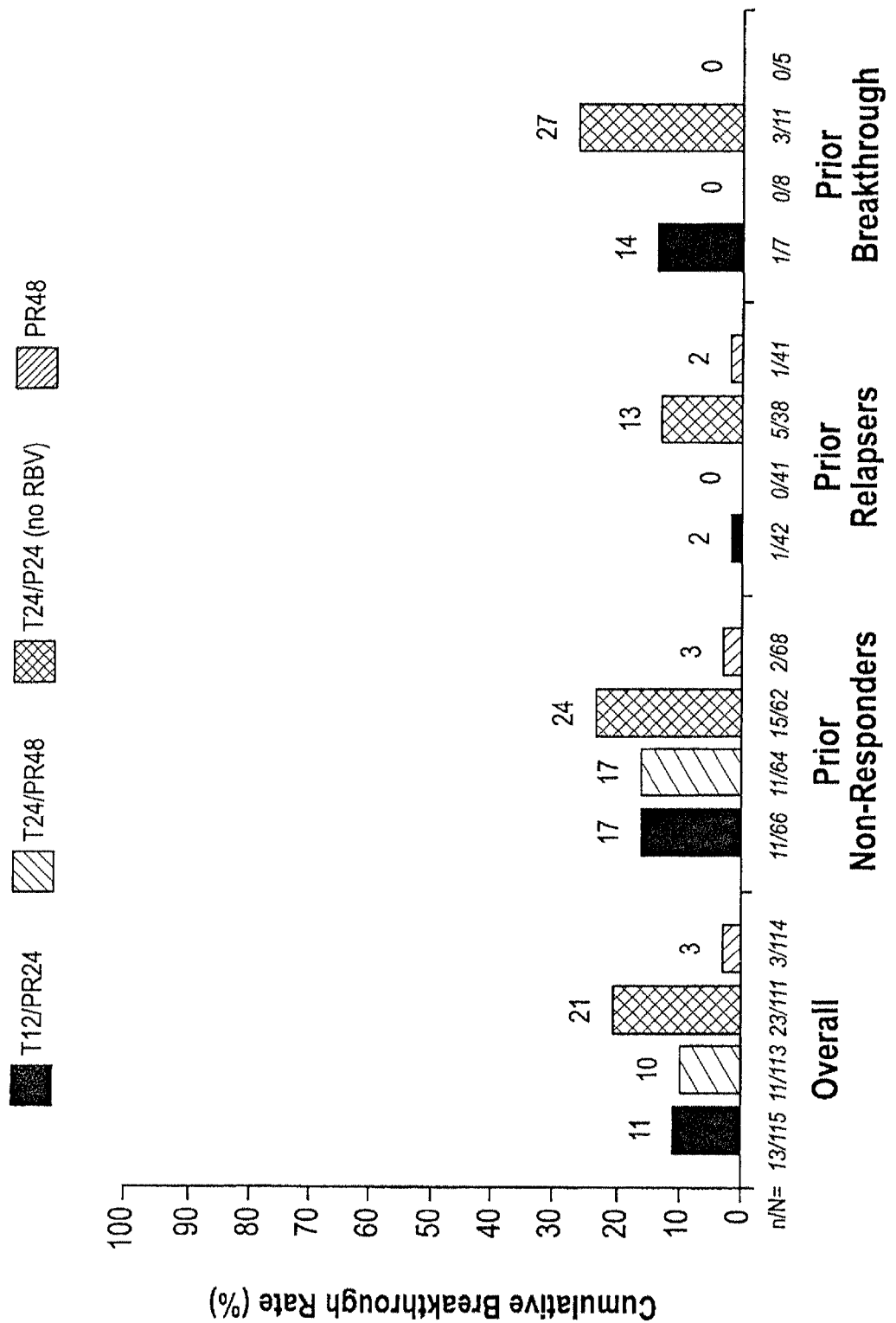
FIG. 17 depicts cumulative viral breakthrough rate from Week 4 through Week 24 by treatment group (ITT).

Overall SVR rates in T12/PR24 and T24/PR48 aims were 51-52% versus 14% in the control arm. Specifically, overall SVR rates in T12/PR24 and T24/PR48 arm in previous non-responders were 38-39% versus 9% in the control arm; in previous relapsers were 69-76% versus 20% in the control aim; and in patients with cirrhosis were 45-54% versus 8% in the control arm. SVR rates in patients who completed assigned treatment are shown in FIG. 13. SVR rates in patients with and without cirrhosis are shown in FIG. 14. Rates for undetectable HCV RNA at Week 4 (rapid viral response (RVR) demonstrated by achieving undetectable HCV RNA 4 weeks after starting study treatment) in prior non-responders and prior relapsers are shown in FIG. 15. Relapse rates for the patients who had undetectable HCV-RNA at the last dose of treatment (overall) and for the patients who had undetectable HCV-RNA at the last dose after the completion of the assigned treatment (completed regimen) are shown in FIG. 16. Cumulative viral breakthrough rates from Week 4 through Week 24 by the treatment group (intent-to-treat (ITT) analysis) are shown in FIG. 17.

Other Embodiments

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments that have been represented by way of example above.

What is claimed is:

1. A therapeutic regimen for treating Hepatitis C virus infection in a patient who failed to achieve a sustained virologic response with prior treatment with pegylated interferon and ribavirin comprising administering to the patient VX-950, or a pharmaceutically acceptable salt thereof, pegylated interferon and ribavirin in an initial phase of about 12 or 24 weeks and pegylated interferon and ribavirin in a secondary phase of about 12, 24 or 36 weeks, wherein the VX-950 administered in the initial phase is in an amount of 750 mg three times per day and the pegylated interferon administered in the initial phase and in the secondary phase is in an amount of 180 µg per week.

2. The therapeutic regimen of claim 1, further comprising administering an immunomodulatory agent, an antiviral agent, another inhibitor of HCV NS3/4A protease, an inhibitor of a target in the HCV life cycle other than NS3/4A protease, an inhibitor of internal ribosome entry, a broad-spectrum viral inhibitor, another cytochrome P-450 inhibitor, an inhibitor of viral cellular entry, or a combination thereof.

3. The therapeutic regimen of claim 2, wherein said immunomodulatory agent is α-, β-, or γ-interferon or thymosin; the antiviral agent is ribavirin, amantadine, or telbivudine; and the inhibitor of another target in the HCV life cycle is an inhibitor of HCV helicase, polymerase, or metalloprotease.

4. The therapeutic regimen of claim 1, wherein the patient who failed to achieve a sustained virologic response with prior treatment with pegylated interferon and ribavirin is a week 4 null responder.

5. The therapeutic regimen of claim 1, wherein the patient who failed to achieve a sustained virologic response with prior treatment with pegylated interferon and ribavirin is a week 12 null responder.

6. The therapeutic regimen of claim 1, wherein the patient who failed to achieve a sustained virologic response with prior treatment with pegylated interferon and ribavirin is a partial responder.

SEQUENCE LISTING

```
<160> NUMBER OF SEQ ID NOS: 1

<210> SEQ ID NO 1
<211> LENGTH: 10
<212> TYPE: PRT
<213> ORGANISM: Hepatitis C virus
<220> FEATURE:
<221> NAME/KEY: PEPTIDE
<222> LOCATION: (1)..(10)
<223> OTHER INFORMATION: Xaa is Abu (aminobutyric acid).

<400> SEQUENCE: 1

Glu Asp Val Val Xaa Cys Ser Met Ser Tyr
1               5                   10
```

7. The therapeutic regimen of claim 1, wherein the patient who failed to achieve a sustained virologic response with prior treatment with pegylated interferon and ribavirin is a breakthrough responder.

* * * * *